(12) United States Patent
Tsuruno et al.

(10) Patent No.: US 10,086,405 B2
(45) Date of Patent: Oct. 2, 2018

(54) PIEZOELECTRIC ELEMENT, PIEZOELECTRIC DEVICE, PROBE, ELECTRONIC MACHINE, AND ULTRASONIC IMAGE APPARATUS

(71) Applicant: SEIKO EPSON CORPORATION, Tokyo (JP)

(72) Inventors: Jiro Tsuruno, Nagano (JP); Tsukasa Funasaka, Nagano (JP); Tomoaki Nakamura, Nagano (JP); Hiromu Miyazawa, Nagano (JP); Hiroshi Ito, Nagano (JP); Masayoshi Yamada, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 688 days.

(21) Appl. No.: 14/669,123

(22) Filed: Mar. 26, 2015

(65) Prior Publication Data

US 2015/0273526 A1    Oct. 1, 2015

(30) Foreign Application Priority Data

Mar. 27, 2014    (JP) .................................. 2014-065114
Feb. 5, 2015    (JP) .................................. 2015-021194

(51) Int. Cl.
    *A61B 8/14*    (2006.01)
    *B06B 1/06*    (2006.01)
    *A61B 8/00*    (2006.01)

(52) U.S. Cl.
    CPC .............. *B06B 1/0666* (2013.01); *A61B 8/14* (2013.01); *A61B 8/4488* (2013.01); *A61B 8/4494* (2013.01); *B06B 1/067* (2013.01); *B06B 1/0629* (2013.01); *B06B 1/0662* (2013.01); *A61B 8/462* (2013.01)

(58) Field of Classification Search
    CPC ..... B06B 1/0666; B06B 1/0662; B06B 1/067; B06B 1/0629; A61B 8/4494; A61B 8/14; A61B 8/4488; A61B 8/462
    USPC .................................................. 600/437–469
    See application file for complete search history.

(56) References Cited

U.S. PATENT DOCUMENTS

| | | | |
|---|---|---|---|
| 9,039,625 B2 * | 5/2015 | Takahashi ............ | A61B 8/4444 600/437 |
| 2002/0105250 A1 | 8/2002 | Klee et al. | |
| 2006/0186762 A1 * | 8/2006 | Sugiura ................. | B06B 1/0692 310/328 |
| 2010/0148627 A1 | 6/2010 | Funasaka et al. | |
| 2010/0259127 A1 * | 10/2010 | Zaitsu ................... | B06B 1/0292 310/300 |

(Continued)

FOREIGN PATENT DOCUMENTS

| | | |
|---|---|---|
| JP | 2002-271897 A | 9/2002 |
| JP | 2010-165341 A | 7/2010 |
| JP | 2010-210283 A | 9/2010 |

*Primary Examiner* — Sanjay Cattungal

(57) ABSTRACT

A piezoelectric element includes a vibrating film, a piezoelectric body, a first electrode, a second electrode, and a groove. The piezoelectric body is arranged upon the vibrating film. The first electrode is arranged upon the piezoelectric body. The second electrode is arranged upon the piezoelectric body and at a position that is separated from the first electrode. The groove is located between the first electrode and the second electrode and splits a surface of the piezoelectric body in two, as seen in plan view from a thickness direction of the vibrating film.

27 Claims, 17 Drawing Sheets

(56) References Cited

U.S. PATENT DOCUMENTS

| | | | |
|---|---|---|---|
| 2012/0323514 A1* | 12/2012 | Nakazawa | G01B 17/00 702/65 |
| 2014/0070668 A1* | 3/2014 | Ona | B06B 1/0629 310/334 |
| 2014/0269220 A1* | 9/2014 | Tamura | H03H 9/21 368/47 |
| 2017/0095838 A1* | 4/2017 | Nakamura | B06B 1/0629 |

* cited by examiner

PIEZOELECTRIC ELEMENT, PIEZOELECTRIC DEVICE, PROBE, ELECTRONIC MACHINE, AND ULTRASONIC IMAGE APPARATUS

CROSS-REFERENCE TO RELATED APPLICATIONS

This application claims priority to Japanese Patent Application No. 2014-065114 filed on Mar. 27, 2014 and Japanese Patent Application No. 2015-021194 filed on Feb. 5, 2015. The entire disclosures of Japanese Patent Application Nos. 2014-065114 and 2015-021194 are hereby incorporated herein by reference.

BACKGROUND

Technical Field

The present invention relates to a piezoelectric element, a piezoelectric device comprising same, a probe, electronic machine, and ultrasonic image apparatus utilizing same, and the like.

Related Art

As is disclosed in Japanese laid-open patent publication No. 2002-271897, a thin-film ultrasonic transducer element is well known. The ultrasonic transducer element is provided with a vibrating film. A piezoelectric film is overlaid on the vibrating film. A first electrode and a second electrode are overlaid on a surface of the piezoelectric film. The piezoelectric film is formed with a uniform thickness.

When a piezoelectric body is easily distorted, the amount of distortion is increased with respect to ultrasonic waves, and so too is the generated voltage increased. Provided that this distortion is constant, the generated voltage increases in proportion to the thickness of the piezoelectric film held between the electrodes. When the thickness of the piezoelectric film increases, however, then a problem emerges in that cracking more readily enters the piezoelectric film in the manufacturing process.

SUMMARY

In view of these circumstances, there is a desire for a piezoelectric element with which it is possible to avoid cracking of the piezoelectric body and possible to maximize the piezoelectric effect of the piezoelectric body.

One aspect of the invention relates to a piezoelectric element provided with: a vibrating film; a piezoelectric body arranged upon the vibrating film; a first electrode arranged upon the piezoelectric body; a second electrode arranged upon the piezoelectric body and at a position that is separated from the first electrode; and a groove located between the first electrode and the second electrode and splitting a surface of the piezoelectric body in two, as seen in plan view from a thickness direction of the vibrating film.

When ultrasonic waves act on the vibrating film, the vibrating film vibrates ultrasonically. Distortion of the piezoelectric body is induced in accordance with the ultrasonic vibration of the vibrating film. The distortion of the piezoelectric body produces a voltage between the electrodes, on the basis of a piezoelectric effect. When the distance between the first electrode and the second electrode, which are arranged in the horizontal direction with respect to the piezoelectric film, is increased, then the generated voltage is increased even without involving an increase in the thickness of the piezoelectric film. At this time, the thickness of the piezoelectric body is reduced by the action of the groove. A deflection resistance of the vibrating film is reduced and the distortion generated between the electrodes is increased in accordance with the reduction of thickness, and therefore a large voltage is produced. Additionally, in the piezoelectric element, the voltage is applied in parallel to the surface of the piezoelectric body, and therefore polarization more fully remains in the piezoelectric body as compared to a case where the voltage is applied perpendicular to the surface. As a result thereof, the application of a polarization voltage can be omitted (or can be reduced) at the time of generation of the piezoelectric effect. In particular, the piezoelectric body has a decrease in thickness localized to the groove, and therefore the distortion of the piezoelectric body is concentrated to between the first electrode and the second electrode, thus making it possible for the piezoelectric effect to be utilized efficiently.

In another aspect of the invention, the groove extends toward an edge of the piezoelectric body, outwardly from between the first electrode and the second electrode, and traverses across one surface of the piezoelectric body. The groove traverses completely across the one surface, from the edge of the piezoelectric body, and therefore the distortion of the piezoelectric body is increased to a maximum limit. The generated voltage is increased to a maximum limit.

In another aspect of the invention, the groove extends toward an edge of the piezoelectric body, outwardly from between the first electrode and the second electrode, and is interrupted between the edge of the piezoelectric body and a space between the first electrode and the second electrode. In this manner, the groove does not completely traverse across the one surface of the piezoelectric body. The piezoelectric body has a decrease in thickness locally between the electrodes, and therefore the distortion is increased between the electrodes, thus making it possible for the piezoelectric effect to be utilized efficiently.

In another aspect of the invention, the groove extends along a hypothetical straight line that passes through a center of gravity of the vibrating film as seen in the plan view. At the vibrating film, greater proximity to the center-of-gravity position means greater deflection during the ultrasonic vibration. Thus, the generated voltage is increased when the groove is arranged at a more readily deflected position.

In another aspect of the invention, the vibrating film is formed in a shape of a rectangle as seen in the plan view, and the groove extends in parallel to any one side of the rectangle. The deflection of the vibrating film maximizes at intermediate positions of equidistance from the two sides extending in parallel to one another. Thus, the generated voltage is increased when the groove extends at a more readily deflected position.

In another aspect of the invention, the piezoelectric body is formed in line symmetry with respect to the hypothetical straight line as seen in the plan view. The behavior of the piezoelectric body maintains the symmetry. As such, the behavior of the piezoelectric body is stabilized during the vibration of the vibrating film.

In another aspect of the invention, a protective film having a lower Young's modulus than the piezoelectric body is formed on the groove. In this manner, the piezoelectric body is protected from, for example, water and the like. The vibration of the vibrating film is not hindered because the protective film has a lower Young's modulus than that of the piezoelectric body.

In another aspect of the invention, the protective film is an acoustic matching layer with which the groove is filled. In this manner, an acoustic matching layer is able to double as the protective film.

In another aspect of the invention, a width of the first electrode along a longitudinal direction of the groove and a width of the second electrode along the longitudinal direction of the groove as seen in the plan view are smaller than a width of the piezoelectric body along the longitudinal direction of the groove as seen in the plan view. Overlapping of the first electrode and the second electrode with the edge of the vibrating film is avoided as much as possible. The first electrode and the second electrode do not hinder the vibration of the vibrating film.

In another aspect of the invention, the piezoelectric body is arranged only within a region of the vibrating film, as seen in the plan view. The piezoelectric body does not hinder the vibration of the vibrating film.

In another aspect of the invention, a relation of $$0.2 \leq \frac{t_1}{t_2} < 1.0$$

holds true between $t_1$ that is a thickness of the piezoelectric body defined with the groove in the thickness direction, and $t_2$ that is a thickness of the piezoelectric body defined elsewhere other than the groove in the thickness direction.

According to verification by the present inventors, when this relationship holds true, the distortion is concentrated in the groove and the effect of the groove is achieved.

In another aspect of the invention, a relationship of $$0.3 \leq \frac{t_1}{t_2} \leq 0.6$$

further holds true between the $t_1$ and the $t_2$.

It has been confirmed that when this relationship holds true, the groove 64 contributes effectively to enhancing the reception sensitivity.

In another aspect of the invention, a relationship of $$0.4 \leq \frac{t_1}{t_2}$$

further holds true between the $t_1$ and the $t_2$.

Provided that the thickness ratio is set at 0.4 or higher, the throughput can be maximally improved.

The piezoelectric element can be utilized by being incorporated into a piezoelectric device. At this time, the piezoelectric device may be provided with: the piezoelectric element; a second vibrating film; a second piezoelectric body arranged upon the second vibrating film; a third electrode arranged upon the second piezoelectric body; a fourth electrode arranged upon the second piezoelectric body and at a position that is separated from the third electrode; a second groove located between the third electrode and the fourth electrode and splitting a surface of the second piezoelectric body in two, as seen in plan view from a thickness direction of the second vibrating film; and an electroconductor section electrically connecting the second electrode and the third electrode together. Two piezoelectric elements are connected in series, and therefore the voltage generated by deformation is increased and the sensitivity is enhanced.

The piezoelectric element can be utilized by being incorporated into a piezoelectric device. At this time, the piezoelectric device may be provided with: the piezoelectric element; a second vibrating film; a third electrode arranged upon the second vibrating film; a second piezoelectric body arranged upon the third electrode; and a fourth electrode arranged upon the second piezoelectric body. The piezoelectric element formed of the vibrating film, the piezoelectric body, the first electrode, and the second electrode can be utilized in receiving sound waves, and a piezoelectric element formed of the second vibrating film, the second piezoelectric body, the third electrode, and the fourth electrode can be utilized in emitting sound waves. The former piezoelectric element has higher sensitivity than the latter piezoelectric element, and therefore the resolution of the sound waves is enhanced.

The piezoelectric element can be utilized by being incorporated into a probe. At this time, the probe may have a plurality of the piezoelectric elements. When the distance between the first electrode and the second electrode, which are arranged in the horizontal direction with respect to the piezoelectric film, is increased, then the generated voltage is increased even without involving an increase in the thickness of the piezoelectric film. At this time, the thickness of the piezoelectric body is reduced by the action of the groove. A deflection resistance of the vibrating film is reduced and the distortion generated between the electrodes is increased in accordance with the reduction of thickness, and therefore a large voltage is produced. Additionally, in the piezoelectric element, the voltage is applied in parallel to the surface of the piezoelectric body, and therefore polarization more fully remains in the piezoelectric body as compared to a case where the voltage is applied perpendicular to the surface. As a result thereof, the application of a polarization voltage can be omitted (or can be reduced) at the time of generation of the piezoelectric effect.

The piezoelectric device can be utilized by being incorporated into a probe. At this time, the probe may comprise a plurality of piezoelectric devices. In the probe, two piezoelectric elements are connected in series, and therefore the voltage generated by deformation is increased and the sensitivity is enhanced.

The piezoelectric device can be utilized by being incorporated into a probe. At this time, the probe may comprise a plurality of piezoelectric devices. The piezoelectric element formed of the vibrating film, the piezoelectric body, the first electrode, and the second electrode can be utilized in receiving sound waves, and a piezoelectric element formed of the second vibrating film, the second piezoelectric body, the third electrode, and the fourth electrode can be utilized in emitting sound waves. The former piezoelectric element has higher sensitivity than the latter piezoelectric element, and therefore the resolution of the sound waves is enhanced.

The piezoelectric element can be utilized by being incorporated into an electronic machine. At this time, the electronic machine may comprise a plurality of piezoelectric elements. When the distance between the first electrode and the second electrode, which are arranged in the horizontal direction with respect to the piezoelectric film, is increased, then the generated voltage is increased even without involving an increase in the thickness of the piezoelectric film. At this time, the thickness of the piezoelectric body is reduced by the action of the groove. A deflection resistance of the vibrating film is reduced and the distortion generated between the electrodes is increased in accordance with the reduction of thickness, and therefore a large voltage is produced. Additionally, in the piezoelectric element, the voltage is applied in parallel to the surface of the piezoelectric body, and therefore polarization more fully remains in the piezoelectric body as compared to a case where the voltage is applied perpendicular to the surface. As a result thereof, the application of a polarization voltage can be omitted (or can be reduced) at the time of generation of the piezoelectric effect.

The piezoelectric device can be utilized by being incorporated into an electronic machine. At this time, the electronic machine may comprise a plurality of piezoelectric devices. In the electronic machine, two piezoelectric elements are connected in series, and therefore the voltage generated by deformation is increased and the sensitivity is enhanced.

The piezoelectric device can be utilized by being incorporated into an electronic machine. At this time, the electronic machine may comprise a plurality of piezoelectric devices. The piezoelectric element formed of the vibrating film, the piezoelectric body, the first electrode, and the second electrode can be utilized in receiving sound waves, and a piezoelectric element formed of the second vibrating film, the second piezoelectric body, the third electrode, and the fourth electrode can be utilized in emitting sound waves. The former piezoelectric element has higher sensitivity than the latter piezoelectric element, and therefore the resolution of the sound waves is enhanced.

The electronic machine may be provided with: a polarization circuit connected to the piezoelectric elements and configured to supply a polarization voltage to the piezoelectric elements; a receiver circuit connected to the piezoelectric elements and configured to receive a voltage on the basis of a piezoelectric effect from the piezoelectric elements; and a switch configured to switch connections of the polarization circuit and the receiver circuit to the piezoelectric element. In this manner, the piezoelectric elements are polarized as appropriate, in accordance with need. The polarization state is maintained properly, and therefore the sensitivity is maintained properly.

The piezoelectric element can be utilized by being incorporated into an ultrasonic image apparatus. At this time, the ultrasonic image apparatus may be provided with a plurality of the piezoelectric elements. When the distance between the first electrode and the second electrode, which are arranged in the horizontal direction with respect to the piezoelectric film, is increased, then the generated voltage is increased even without involving an increase in the thickness of the piezoelectric film. At this time, the thickness of the piezoelectric body is reduced by the action of the groove. A deflection resistance of the vibrating film is reduced and the distortion generated between the electrodes is increased in accordance with the reduction of thickness, and therefore a large voltage is produced. Additionally, in the piezoelectric element, the voltage is applied in parallel to the surface of the piezoelectric body, and therefore polarization more fully remains in the piezoelectric body as compared to a case where the voltage is applied perpendicular to the surface. As a result thereof, the application of a polarization voltage can be omitted (or can be reduced) at the time of generation of the piezoelectric effect.

The piezoelectric device can be utilized by being incorporated into an ultrasonic image apparatus. At this time, the ultrasonic image apparatus may be provided with a plurality of piezoelectric devices. In the ultrasonic image apparatus, two piezoelectric elements are connected in series, and therefore the voltage generated by deformation is increased and the sensitivity is enhanced.

The piezoelectric device can be utilized by being incorporated into an ultrasonic image apparatus. At this time, the ultrasonic image apparatus may be provided with a plurality of piezoelectric devices. The piezoelectric element formed of the vibrating film, the piezoelectric body, the first electrode, and the second electrode can be utilized in receiving sound waves, and a piezoelectric element formed of the second vibrating film, the second piezoelectric body, the third electrode, and the fourth electrode can be utilized in emitting sound waves. The former piezoelectric element has higher sensitivity than the latter piezoelectric element, and therefore the resolution of the sound waves is enhanced.

The ultrasonic image apparatus may be provided with: a polarization circuit connected to the piezoelectric elements and configured to supply a polarization voltage to the piezoelectric elements; a receiver circuit connected to the piezoelectric elements and configured to receive a voltage on the basis of a piezoelectric effect from the piezoelectric elements; and a switch configured to switch the connections of the polarization circuit and the receiver circuit to the piezoelectric element. In this manner, the piezoelectric elements are polarized as appropriate, in accordance with need. The polarization state is maintained properly, and therefore the sensitivity is maintained properly.

Another aspect of the invention relates to a piezoelectric element, provided with: a vibrating film; a piezoelectric body arranged upon the vibrating film; a first signal electrode arranged upon one surface of the piezoelectric body; a second signal electrode arranged upon the one surface of the piezoelectric body and at a position that is separated from the first signal electrode; and a groove located between the first signal electrode and the second signal electrode as seen in plan view from a thickness direction of the vibrating film, and reducing the thickness of the piezoelectric body in a direction orthogonal to a surface of the vibrating film.

When ultrasonic waves act on the vibrating film, the vibrating film vibrates ultrasonically. Distortion of the piezoelectric body is induced in accordance with the ultrasonic vibration of the vibrating film. The distortion of the piezoelectric body produces a voltage between the electrodes, on the basis of a piezoelectric effect. When the distance between the first electrode and the second electrode, which are arranged in the horizontal direction with respect to the piezoelectric film, is increased, then the generated voltage is increased even without involving an increase in the thickness of the piezoelectric film. At this time, the thickness of the piezoelectric body is reduced by the action of the groove. A deflection resistance of the vibrating film is reduced and the distortion generated between the electrodes is increased in accordance with the reduction of thickness, and therefore a large voltage is produced. Additionally, in the piezoelectric element, the voltage is applied in parallel to the surface of the piezoelectric body, and therefore polarization more fully remains in the piezoelectric body as compared to a case where the voltage is applied perpendicular to the surface. As a result thereof, the application of a polarization voltage can be omitted (or can be reduced) at the time of generation of the piezoelectric effect. In particular, the piezoelectric body has a decrease in thickness localized to the groove, and therefore the distortion of the piezoelectric body is concentrated to between the first electrode and the second electrode, thus making it possible for the piezoelectric effect to be utilized efficiently.

BRIEF DESCRIPTION OF THE DRAWINGS

Referring now to the attached drawings which form a part of this original disclosure.

DETAILED DESCRIPTION OF EXEMPLARY EMBODIMENTS

The following describes embodiments of the present invention, with reference to the accompanying drawings. The present embodiments described below are not, however, meant to improperly limit the content of the present invention set forth in the claims, nor is the entire configuration described in the present embodiments necessarily essential in terms of the solution of the present invention.

(1) Overall Configuration of Ultrasonic Diagnostic Apparatus

Figure 1:
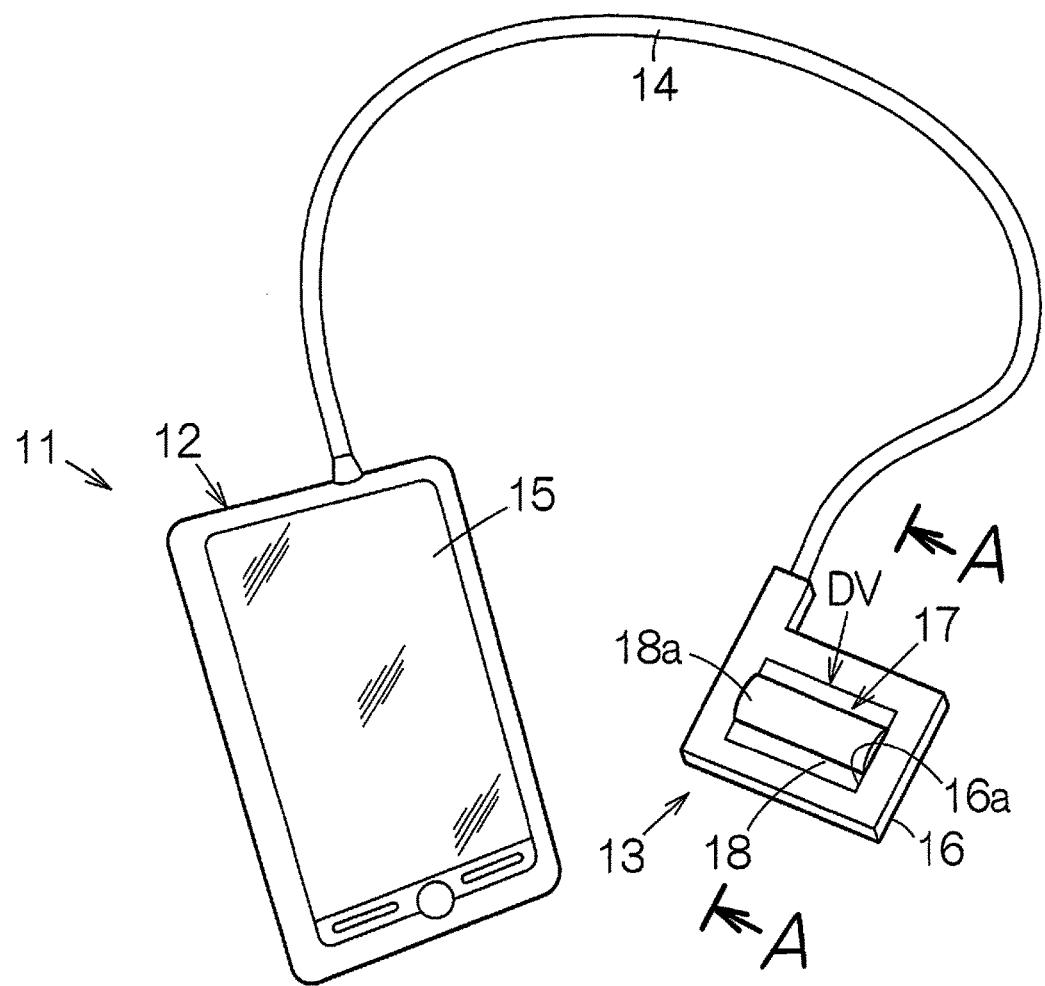
FIG. 1 is an external view schematically illustrating one specific example of an electronic machine as in an embodiment, namely, an ultrasonic diagnostic apparatus.

FIG. 1 schematically illustrates the configuration of one specific example of an electronic machine as in an embodiment, namely, an ultrasonic diagnostic apparatus (ultrasonic image apparatus) 11. The ultrasonic diagnostic apparatus 11 is provided with an apparatus terminal (processing unit) 12 and an ultrasonic probe (probe) 13. The apparatus terminal 12 and the ultrasonic probe 13 are connected to each other with a cable 14. The apparatus terminal 12 and the ultrasonic probe 13 exchange electrical signals with each other through the cable 14. A display panel (display device) 15 is incorporated into the apparatus terminal 12. A screen of the display panel 15 is exposed on the surface of the apparatus terminal 12. At the apparatus terminal 12, an image is generated on the basis of ultrasonic waves detected by the ultrasonic probe 13. A visualized detection result is displayed on the screen of the display panel 15.

The ultrasonic probe 13 has a housing 16. An ultrasonic device unit DV is housed in the housing 16. The ultrasonic device unit DV is provided with an ultrasonic device 17. The ultrasonic device 17 is provided with an acoustic lens 18. An outer surface of the acoustic lens 18 is formed of a partial cylindrical surface 18a. The acoustic lens 18 is formed of, for example, a silicone resin. The acoustic lens 18 has an acoustic impedance that is close to the acoustic impedance of a living body. A window hole 16a is demarcated in the housing 16. The acoustic lens 18 is arranged in the window hole 16a. The outer surface of the acoustic lens 18 is exposed at the surface of the housing 16. The ultrasonic device 17 outputs ultrasonic waves from the surface, and also receives reflected waves of the ultrasonic waves.

(2) Configuration of Ultrasonic Device Unit

Figure 2:
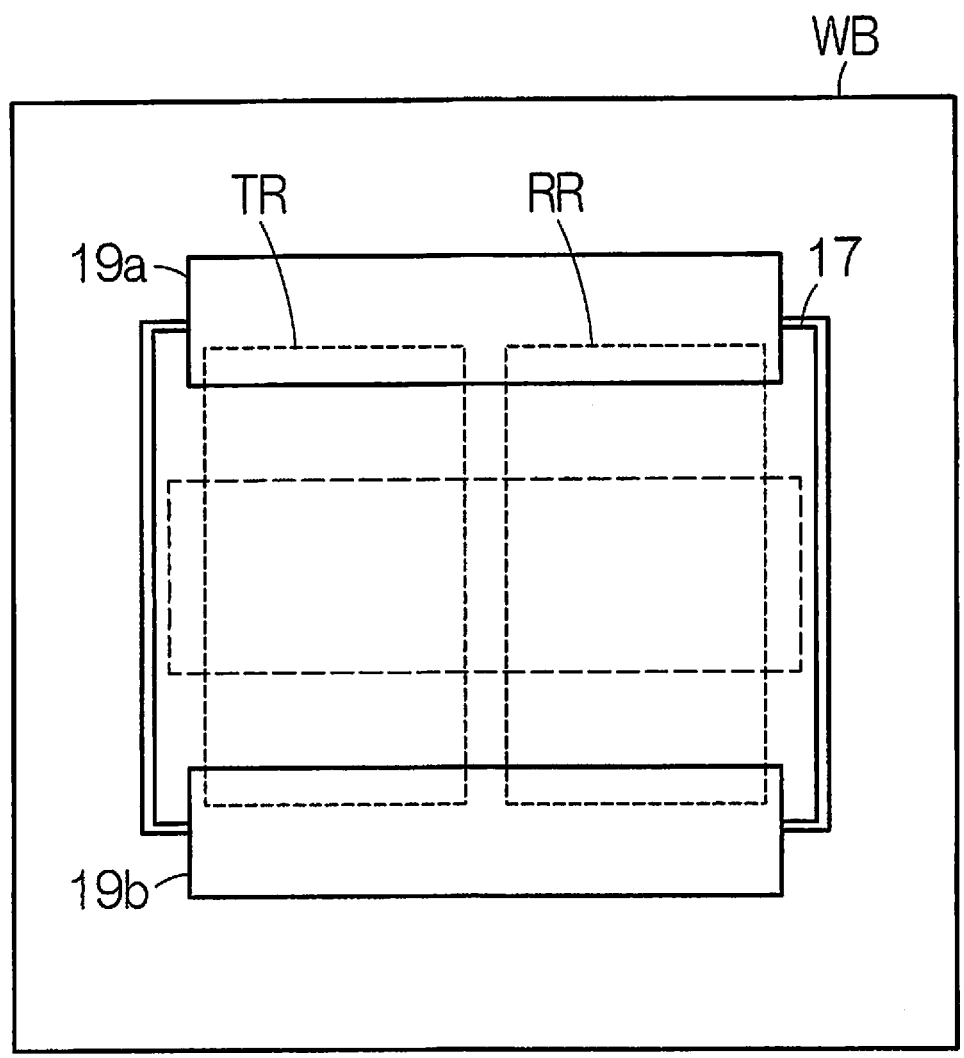
FIG. 2 is an enlarged plan view schematically illustrating the configuration of an ultrasonic device unit.

As is illustrated in FIG. 2, the ultrasonic device unit DV is provided with a wiring board WB. The ultrasonic device 17 is mounted onto the wiring board WB. In this mounting, a depression for accepting the ultrasonic device 17 may be formed on the surface of the wiring board WB. It suffices for the depression to be hollowed from the plane of the wiring board WB. The ultrasonic device 17 can be fixed to the wiring board WB with, for example, a resin material.

A receiving array RR and a transmission array TR are formed in the ultrasonic device 17. The receiving array RR is constituted of an arraying of first ultrasonic transducer elements (hereinafter "first piezoelectric elements) arranged in the form of an array, as shall be described below. The transmission array TR is constituted of an arraying of second ultrasonic transducer elements (hereinafter "second piezoelectric elements) arranged in the form of an array, as shall be described below. The receiving array RR and the transmission array TR are electrically connected to a wiring pattern (not shown) on the wiring board with a first flexible printed wiring board (hereinafter a "first wiring board") 19a and a second flexible printed wiring board (hereinafter a "second wiring board") 19b. The wiring pattern is connected to a connector on a reverse surface of the wiring board WB. The cable 14 is formed of a wiring that is connected to the connector.

(3) Configuration of Transmission Array

Figure 3:
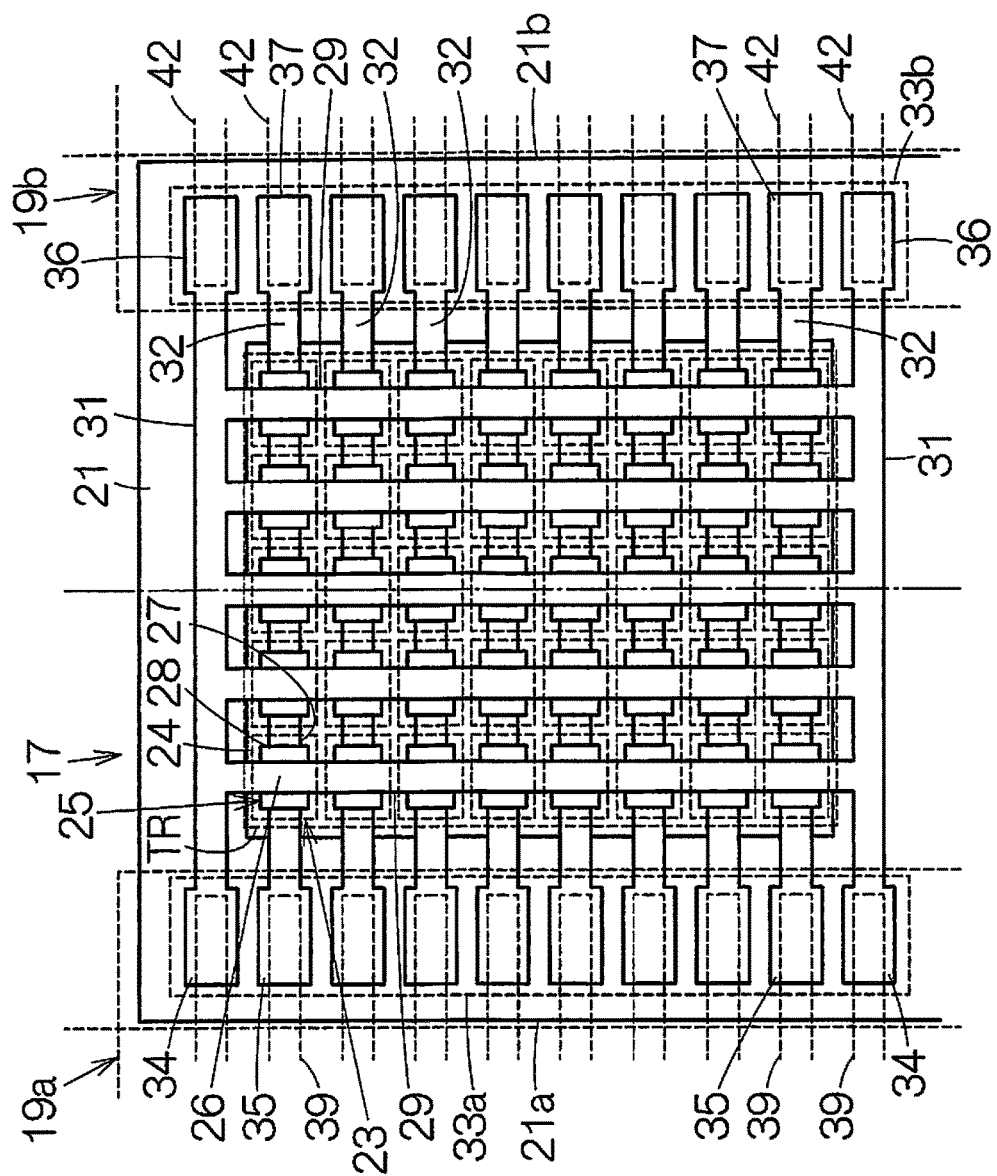
FIG. 3 is an enlarged partial plan view of an ultrasonic device schematically illustrating a region of a transmission array.

FIG. 3 relates to a region of the transmission array TR, and schematically illustrates a plan view of the ultrasonic device 17. The ultrasonic device 17 is provided with a base 21. The transmission array TR is formed on a surface of the base 21. An arraying of second piezoelectric elements 23 is formed of a matrix of a plurality of columns and a plurality of rows. Otherwise, a staggered arrangement may also be established in the array. With a staggered arrangement, it suffices for a second piezoelectric element 23 group of even-numbered row to be offset by one-half a column pitch with respect to a second piezoelectric element 23 group of odd-numbered rows. The number of elements of one among either the odd-numbered rows or the even-numbered rows may be one fewer than the number of elements in the other.

Each of the second piezoelectric elements 23 is provided with a vibrating film 24. In FIG. 3, outlines of the vibrating films 24 are drawn with dotted lines in plan view of a direction orthogonal to film surfaces of the vibrating films 24 (plan view from a thickness direction of the wiring board. Oscillators 25 are formed on the vibrating films 24. The oscillators 25 are constituted of an upper electrode (fourth electrode) 26, a lower electrode (third electrode) 27, and a piezoelectric film (a second piezoelectric body) 28. For each of the second piezoelectric elements 23, the lower electrode 27 is arranged upon the vibrating film 24, the piezoelectric film 28 is arranged upon the lower electrode 27, and the upper electrode 26 is arranged upon the piezoelectric film 28. The upper electrode 26, the lower 27, and the piezoelectric film 28 are overlaid in the order of lower electrode 27, then piezoelectric film 28, and finally upper electrode 26. Thus, the piezoelectric film 28 is sandwiched between the upper electrode 26 and the lower electrode 27.

A plurality of first electroconductors 29 are formed on the surface of the base 21. The first electroconductors 29 extend in parallel to one another in a column direction of the arraying. One first electroconductor 29 is allocated to each one of the columns of the second piezoelectric elements 23. One first electroconductor 29 is connected in common to the piezoelectric films 28 of the second piezoelectric elements 23 that are aligned side by side in the column direction of the arraying. The first electroconductors 29 form the upper electrodes 26 for each of the second piezoelectric elements 23. Two ends of the first electroconductors 29 are each connected to a pair of lead wirings 31. The lead wirings 31 extend in parallel to one another in a row direction of the arraying. As such, all of the first electroconductors 29 have the same length. Thus, the upper electrodes 26 are connected in common to the second piezoelectric elements 23 of the entire matrix. The first electroconductors 29 can be formed of, for example, iridium (Ir). However, another electroconductive material may be utilized for the first electroconductors 29.

A plurality of second electroconductors 32 are formed on the surface of the base 21. The second electroconductors 32 extend in parallel to one another in a column direction of the arraying. One second electroconductor 32 is allocated to each one of the rows of the second piezoelectric elements 23. One second electroconductor 32 is connected in common to the piezoelectric films 28 of the second piezoelectric elements 23 that are aligned side by side in the row direction of the arraying. The second electroconductors 32 form the lower electrodes 27 for each of the second piezoelectric elements 23. For the second electroconductors 32, it would be possible to use, for example, a multilayer film of titanium (Ti), iridium (Ir), platinum (Pt), and titanium (Ti). However, another electroconductive material may be utilized for the second electroconductors 32.

Power distribution to the second piezoelectric elements 23 is switched for each of the rows. Depending on this switching of the power distribution, a linear scan or a sector scan is realized. One row of the second piezoelectric elements 23 outputs the ultrasonic waves at the same time, and therefore the number of individuals in one row, i.e., the number of columns in the arraying can be decided in accordance with the output level of the ultrasonic waves. The number of columns may be set to, for example, about ten to 15. Some being omitted in the drawings, there are five columns drawn. The number of rows in the arraying can be decided in accordance with the spread of the range of the scan. The number of rows may be set to, for example, 128 rows or 256 rows. Some being omitted in the drawings, there are eight rows drawn. The roles of the upper electrodes 26 and the lower electrodes 27 may be interchanged. That is to say, the lower electrodes may be connected in common to the second piezoelectric elements 23 of the entire matrix, the upper electrodes then being connected to the second piezoelectric elements 23 in common for every row of the arraying.

The outline of the base 21 has a first side 21a and a second side 21b, which face one another partitioned with a pair of mutually parallel straight lines. A first terminal array 33a of one line is arranged between the first side 21a and the outline of the transmission array TR. A second terminal array 33b of one line is arranged between the second side 21b and the outline of the transmission array TR. The first terminal array 33a can form one line in parallel with the first side 21a. The second terminal array 33b can form one line in parallel with the second side 21b. The first terminal array 33a is constituted of one pair of upper electrode terminals 34 and a plurality of lower electrode terminals 35. Similarly, the second terminal array 33b is constituted of one pair of upper electrode terminals 36 and a plurality of lower electrode terminals 37. The upper electrode terminals 34, 36 are each connected to the two ends of one lead wiring 31. It suffices for the lead wiring 31 and the upper electrode terminals 34, 36 to be formed in plane symmetry on a vertical plane that bisects the transmission array TR. The lower electrode terminals 35, 37 are each connected to the two ends of one second electroconductor 32. It suffices for the second electroconductor 32 and the lower electrode terminals 35, 37 to be formed in plane symmetry on a vertical plane that bisects the transmission array TR. Herein, the outline of the base 21 is formed in the shape of a rectangle. The outline of the base 21 may also be a square, or may be a trapezoid.

The first wiring board 19a is coupled to the base 21. The first wiring board 19a covers the first terminal array 33a. At one end of the first wiring board 19a, there are electroconductive lines, namely, first signal lines 39 that are formed so as to correspond individually to the upper electrode terminals 34 and the lower electrode terminals 35. The first signal lines 39 are opposed and bonded to the upper electrode terminals 34 and the lower electrode terminals 35, respectively. Similarly, the second wiring board 19b is coupled to the base 21. The second wiring board 19b covers the second terminal array 33b. At one end of the second wiring board 19b, there are electroconductive lines, namely, second signal lines 42 that are formed so as to correspond individually to the upper electrode terminals 36 and the lower electrode terminals 37. The second signal lines 42 are opposed and bonded to the upper electrode terminals 36 and the lower electrode terminals 37, respectively.

Figure 4:
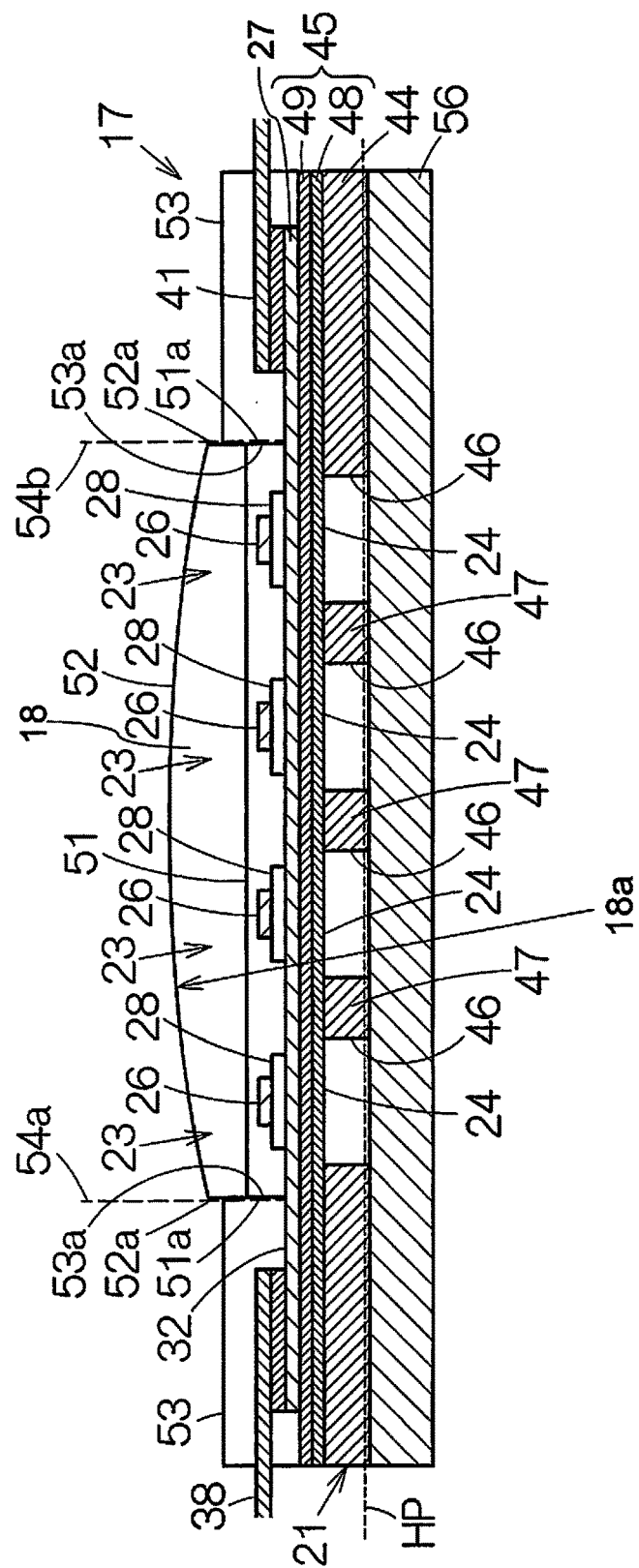
FIG. 4 is an enlarged vertical cross-sectional view taken along the A-A line of FIG. 1.

As illustrated in FIG. 4, the base 21 is provided with a substrate 44 and a coating film 45. The coating film 45 is formed in one surface on the surface of the substrate 44. Opening sections 46 are formed on the substrate 44 for each of the second piezoelectric elements 23. The opening sections 46 are arranged in the form of an array with respect to the substrate 44. An outline of a region where the opening sections 46 are arranged corresponds to the outline of the transmission array TR. Partition walls 47 provide demarcation between two adjacent opening sections 46. Adjacent opening sections 46 are partitioned from one another with the partition walls 47. The wall thickness of the partition walls 47 corresponds to the spacing between the opening sections 46. The partition walls 47 define two wall surfaces within planes stretching in parallel with one another. The wall thickness corresponds to the distance between the two wall surfaces. That is to say, the wall thickness can be defined by the length of a perpendicular line that is orthogonal to the wall surfaces and sandwiched between the wall surfaces. The substrate 44 may be formed of, for example, a silicon substrate.

The coating film 45 is constituted of a silicon oxide ($SiO_2$) layer 48 layered onto the surface of the substrate 44 and a zirconium oxide ($ZrO_2$) layer 49 layered onto the surface of the silicon oxide layer 48. The coating film 45 is in contact with the opening sections 46. Thus, the vibrating films 24 are formed by a part of the coating film 45, in correspondence with the outline of the opening sections 46. The vibrating films 24 are portions of the coating film 45 that face the opening sections 46 and therefore are capable of film vibration in the thickness direction of the substrate 44. The film thickness of the silicon oxide layer 48 can be decided on the basis of the resonance frequency.

The lower electrodes 27, the piezoelectric films 28, and the upper electrodes 26 are layered in the stated order on the surface of the vibrating films 24. The piezoelectric films 28 can be formed of, for example, lead zirconate titanate (PZT). Another piezoelectric material may be used for the piezoelectric films 28. Herein, the piezoelectric films 28 completely cover the second electroconductors 32, beneath the first electroconductors 29. By the action of the piezoelectric films 28, a short circuit between the first electroconductors 29 and the second electroconductors 32 can be avoided.

An acoustic matching layer 51 is layered onto the surface of the base 21. The acoustic matching layer 51 covers the transmission array TR. The film thickness of the acoustic matching layer 51 is decided in accordance with the resonance frequency of the vibrating films 24. For the acoustic matching layer 51, it would be possible to use, for example, a silicone resin film. The acoustic lens 18 is arranged on the acoustic matching layer 51. The acoustic lens 18 is in close contact with the surface of the acoustic matching layer 51. The acoustic lens 18 is adhered to the base 21 by the action of the acoustic matching layer 51. The partial cylindrical surface 18a of the acoustic lens 18 has a generatrix that is parallel to the first electroconductors 29. The curvature of the partial cylindrical surface 18a is decided in accordance with a focal point of the ultrasonic waves that are emitted from one row of the second piezoelectric elements 23 connected to one streak of the second electroconductors 32. The acoustic lens 18 is formed of, for example, a silicone resin. The acoustic lens 18 has an acoustic impedance that is close to the acoustic impedance of a living body.

A protective film 53 is fixed to the base 21. The protective film 53 is formed of, for example, a material that is impermeable to water, such as an epoxy resin. The protective film 53 may also, however, be formed of another resin material. The protective film 53 is in contact with the acoustic lens 18 and with the acoustic matching layer 51. Herein, the protective film 53 sandwiches the acoustic lens 18 and the acoustic matching layer 51 with contact surfaces 53a that respectively run along two virtual planes 54a, 54b which spread in parallel with the generatrix of the acoustic lens 18 and intersect at a right angle with the base 21.

A backing material 56 is fixed to a reverse surface of the base 21. The reverse surface of the base 21 is overlaid onto the surface of the backing material 56. The backing material 56 closes the opening section 46 at a reverse surface of the ultrasonic device 17. The backing material 56 can be provided with a rigid base material. Herein, the partition walls 47 are joined to the backing material 56. The backing material 56 is bonded to each of the partition walls 47 in at least one bonding area. In the bonding, an adhesive can be used.

(4) Configuration of Receiving Array as in First Embodiment

Figure 5:
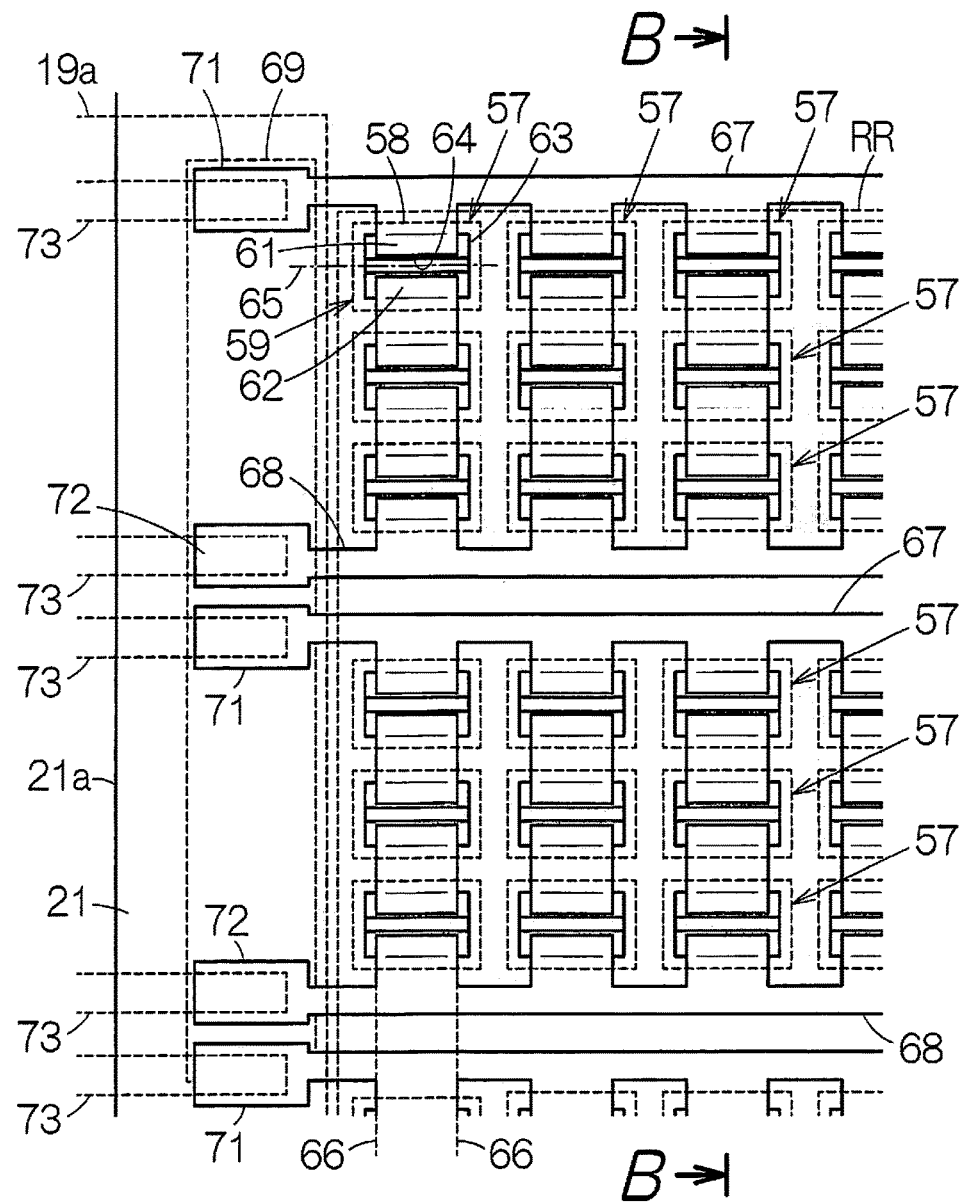
FIG. 5 is an enlarged partial plan view of the ultrasonic device schematically illustrating a region of a receiving array as in a first embodiment.

FIG. 5 relates to a region of the receiving array RR, and schematically illustrates an enlarged partial plan view of the ultrasonic device 17. The receiving array RR is formed on the surface of the base 21. An arraying of first piezoelectric elements 57 is formed of a matrix of a plurality of columns and a plurality of rows. Each of the first piezoelectric elements 57 is provided with a vibrating film 58. In FIG. 5, outlines of the vibrating films 58 are drawn with dotted lines in plan view as seen from a view orthogonal to a film surface of the vibrating films 58 (a plan view as seen from the thickness direction of the wiring board; hereinafter simply called "plan view"). The vibrating films 48 are formed of the coating film 45 of the substrate 44 surface, similarly to the vibrating films 24 described above. Oscillators 59 are formed on the vibrating films 58. The oscillators 59 are constituted of a first electrode 61, a second electrode 62, and a piezoelectric film (piezoelectric body) 63. The first electrodes 61 and the second electrodes 62 are arranged upon the piezoelectric films 63. The second electrodes 62 are arranged upon the piezoelectric films 63 at positions that are separated from the first electrodes 61. Herein, the vibrating films 58 are formed in the shape of rectangles (which includes squares) in plan view.

Grooves 64 are formed between the first electrodes 61 and the second electrodes 62 on the surfaces of the piezoelectric films 63. The grooves 64 extend toward an edge of the piezoelectric films 63, outwardly from between the first electrodes 61 and the second electrodes 62, and traverse across one surface of the piezoelectric films 63. The grooves 64 not only split the surfaces of the piezoelectric films 63 into two between the first electrodes 61 and the second electrodes 62, but also completely traverse across the one surface from edge to edge of the piezoelectric films 63, and therefore split the one surface of the piezoelectric films 63 into two. That is to say, the grooves 64 are provided extending so as to connect two outer edge sections of the surfaces of the piezoelectric films 63. Herein, the grooves 64 extend along straight lines 65 that pass through the centers of gravity of the vibrating films 58 (through the centroid of the outline) in plan view. The straight lines 65 extend in parallel with long sides of the outlines of the vibrating films 58. Herein, the first electrodes 61 and the second electrodes 62 spread on the inside of two virtual vertical planes 66 that are orthogonal to the surfaces of the piezoelectric films 63 and divided one end and the other end of the grooves 64. The piezoelectric films 63 spread on the inside of two outlining lines of the vibrating films 58 that are defined in parallel with the virtual vertical planes 66. As such, the width of the first electrodes 61 along the longitudinal direction of the grooves 64 and the width of the second electrodes 62 along the longitudinal direction of the grooves 64 are smaller than the width of the piezoelectric films 63 along the longitudinal direction of the grooves 64 in plan view. The piezoelectric films 63 are arranged only within the regions of the vibrating films 58 in plan view. The piezoelectric films 63 are formed in line symmetry with respect to the straight lines 65 in plan view.

A plurality of third electroconductors 67 and fourth electroconductors 68 are formed on the surface of the base 21. The third electroconductors 67 and the fourth electroconductors 68 extend in parallel to one another in the row direction of the arraying. The third electroconductors 67 and the fourth electroconductors 68 are arranged alternately. A plurality of columns of the first piezoelectric elements 57 are allocated for every one pair of the third electroconductors 67 and the fourth electroconductors 68 that are adjacent. The first piezoelectric elements 57 are connected in series for each individual column between the third electroconductors 67 and the fourth electroconductors 68. That is to say, with first piezoelectric elements 57 that are adjacent within a column, the second electrode 62 of one element is connected to the first electrode 61 of another element. The same material can be used for the first electrodes 61, the second electrodes 62, the third electroconductors 67, and the fourth electroconductors 68. For example, a multilayer film of titanium (Ti), iridium (Ir), platinum (Pt), and titanium (Ti) could be used for the first electrodes 61, the second electrode 62, the third electroconductors 67, and the fourth electroconductors 68. Other electroconductive materials may be used, however, for the first electrodes 61, the second electrodes 62, the third electroconductors 67, and the fourth electroconductors 68.

One line of a third terminal array 69 is arranged between the first side 21*a* of the base 21 and the outline of the receiving array RR. The third terminal array 69 can form one line in parallel with the first side 21*a*. The third terminal array 69 is constituted of signal terminals 71 and common terminals 72. The signal terminals 71 are connected to the third electroconductors 67. The common terminals 72 are connected to the fourth electroconductors 68. Herein, the third terminal array 69 forms one line along with a first terminal array 33*a*. The first wiring board 19*a* covers the first terminal array 33*a* and the third terminal array 69. At one end of the first wiring board 19*a*, there are electroconductive lines, namely, third signal lines 73 that are formed so as to correspond individually to the signal terminals 71 and the common terminals 72. The third signal lines 73 are opposed and bonded to the signal terminals 71 and the common terminals 72, respectively.

One line of a fourth terminal array (not shown) may similarly be arranged between the second side 21*b* of the base 21 and the outline of the receiving array RR. It suffices for the fourth terminal array to form one line along with the second terminal array 33*b*. The second wiring board 19*b* covers the second terminal array 33 and the fourth terminal array. At one end of the second wiring board 19*b*, there are electroconductive lines, namely, fourth signal lines that are formed so as to correspond individually to signal terminals and common terminals. The fourth signal lines are opposed and bonded to the signal terminals and the common terminals, respectively.

Figure 6:
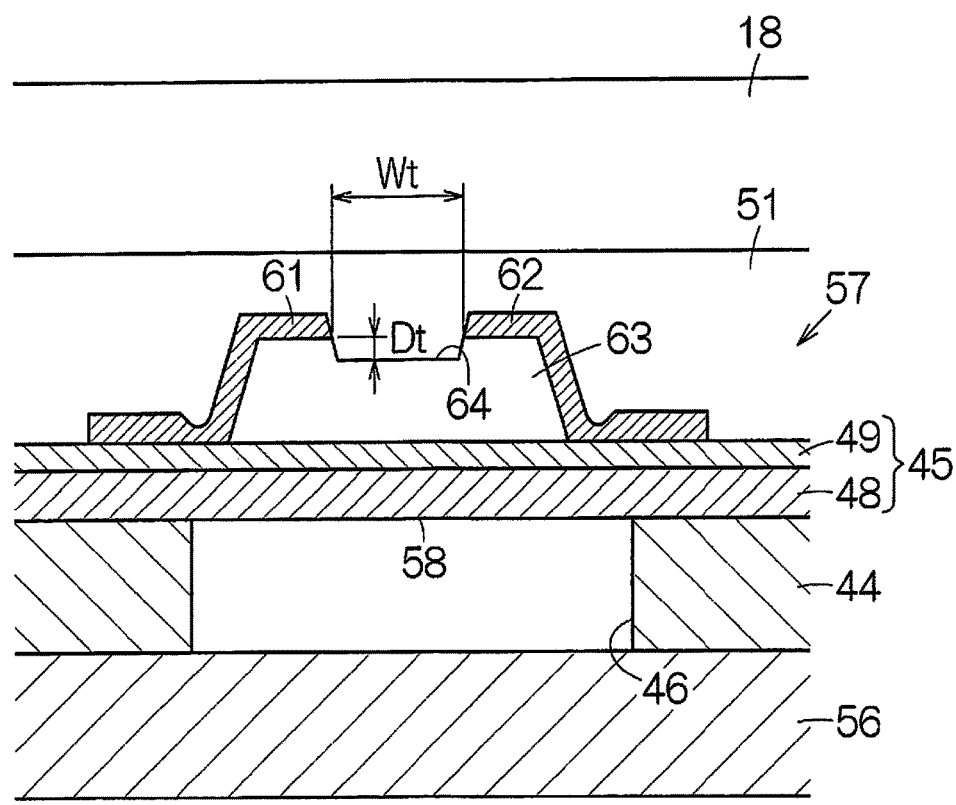
FIG. 6 is a vertical cross-sectional view taken along the B-B line in FIG. 5.

As illustrated in FIG. 6, the opening sections 46 are formed on the base 21 at every one of the first piezoelectric elements 57. The opening sections 46 are arranged in the form of an array with respect to the substrate 44. An outline of a region where the opening sections 46 are arranged corresponds to the outline of the receiving array RR. The vibrating films 58 are formed by a part of the coating film 45, in correspondence with the outline of the opening sections 46. The piezoelectric films 63 are fixed to the surfaces of the vibrating films 58. The piezoelectric films 63 can be formed of, for example, lead zirconate titanate (PZT). Another piezoelectric material may be used for the piezoelectric films 63. At an uppermost surface of the piezoelectric films 63, it suffices for the grooves 64 to have a uniform width Wt and to have a uniform depth Dt. It suffices for the first electrodes 61 and the second electrodes 62 to be interrupted at the edges of the grooves 64. The grooves 64 are filled in with the acoustic matching layer (protective film) 51. The acoustic matching layer 51 has a lower Young's modulus than the piezoelectric films 63. The grooves 64 reduce the thickness of the piezoelectric films 63 in the direction orthogonal to the surfaces of the vibrating films 58.

(5) Operation of Ultrasonic Diagnostic Apparatus

The following is a simple description of the operation of the ultrasonic diagnostic apparatus 11. At the transmission array TR, a pulse signal is supplied to the oscillators 25. The pulse signal passes through the lower electrode terminals 35, 37 and the upper electrode terminals 34, 36 and is supplied to the second piezoelectric elements 23 for each of the rows. At each of the second piezoelectric elements 23, an electric field is applied between the lower electrode 27 and the upper electrode 26. The piezoelectric films 28 vibrate at an ultrasonic frequency. The vibration of the piezoelectric films 28 is transmitted to the vibrating films 24. In this manner, the vibrating films 24 vibrate ultrasonically. As a result thereof, a desired ultrasonic beam is emitted toward a subject (for example, the interior of a human body).

At the receiving array RR, power distribution to the first piezoelectric elements 57 is switched to each one group (plurality of columns) sandwiched between the third electroconductors 67 and the fourth electroconductors 68. For each one group of a plurality of columns, the first piezoelectric elements 57 receive ultrasonic waves. Reflected waves from the ultrasonic waves cause the vibrating films 58 to vibrate. The ultrasonic vibration of the vibrating films 58 causes the piezoelectric films 63 to vibrate ultrasonically at a desired frequency. A voltage is outputted from the oscillators 59 in accordance with a piezoelectric effect of the oscillators 59. At each of the first piezoelectric elements 57, a potential is generated between the first electrodes 61 and the second electrodes 62. The potential is outputted as an electric signal from the signal terminals 71 and the common terminals 72. In this manner, ultrasonic waves are detected.

The ultrasonic waves are repeatedly transmitted and received. As a result thereof, linear scanning or sector scanning is realized. When a scan is complete, an image is formed on the basis of a digital signal of the output signal. The image thus formed is displayed on the screen of the display panel 15.

Figure 7:
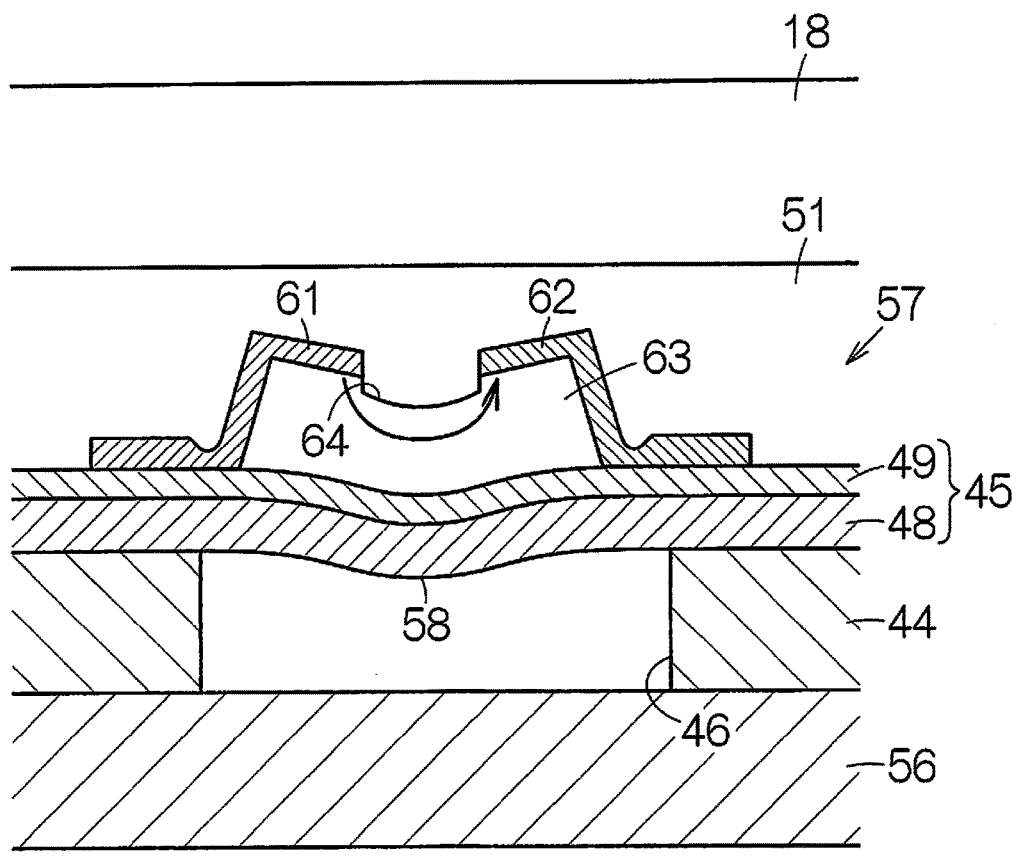
FIG. 7 is a vertical cross-sectional view that corresponds to FIG. 6 and illustrates distortion of a piezoelectric film.

At the first piezoelectric elements 57, when the distance between the first electrodes 61 and the second electrodes 62 increases, there is an increase in a distortion amount of the piezoelectric films 63 even without an accompanying increase in the thickness of the piezoelectric films 63. The generated voltage is increased. At this time, the thickness of the piezoelectric films 63 is reduced by the action of the grooves 64. As illustrated in FIG. 7, a deflection resistance of the vibrating films 58 is reduced and the distortion generated between the electrodes is increased in accordance with the reduction of thickness, and therefore a large voltage is produced. Additionally, at the first piezoelectric elements 57, the voltage is applied in parallel to the surfaces of the piezoelectric films 63, and therefore polarization more fully remains at the piezoelectric films 63 as compared to a case where the voltage is applied perpendicular to the surface. As a result thereof, the application of a polarization voltage can be omitted (or can be reduced) at the time of generation of the piezoelectric effect. In particular, the piezoelectric films 63 have a decrease in thickness localized to the grooves 64, and therefore the distortion of the piezoelectric films 63 is concentrated to the paths of the lines of electric force between the first electrodes 61 and the second electrodes 62, thus making it possible for the piezoelectric effect to be utilized efficiently.

The grooves 64 extend along the straight lines 65 that pass through the centers of gravities of the vibrating films 58 in plan view. At the vibrating films 58, greater proximity to the center-of-gravity position means greater deflection during the ultrasonic vibration. Thus, the generated voltage is increased when the grooves 64 are arranged at more readily deflected positions. In particular, the vibrating films 58 are formed in the shape of a rectangle in plan view. The deflection of the vibrating films 58 maximizes at intermediate positions of equidistance from the two sides extending in parallel to one another. The generated voltage is increased when the grooves 64 extend in parallel to the long sides of the rectangle. Herein, the grooves 64 traverse completely across the one surfaces, from edge to edge of the piezoelectric films 63, and therefore the distortion of the piezoelectric films 63 is increased to a maximum limit. The generated voltage is increased to a maximum limit. The piezoelectric films 63 are formed in line symmetry with respect to the straight lines 65 in plan view, and the behavior of the piezoelectric films 63 maintains the symmetry. As such, the behavior of the piezoelectric films 63 is stabilized during the vibration of the vibrating films 58.

The grooves 64 are filled in with the acoustic matching layer 51. The acoustic matching layer 51 functions as a protective film. In this manner, the piezoelectric films 63 are protected from, for example, water and the like. The acoustic matching layer 51 has a lower Young's modulus than the piezoelectric films 63, and therefore the vibration of the vibrating films 58 is not hindered.

At the first piezoelectric elements 57, the first electrodes 61 and the second electrodes 62 spread on the inside of the two virtual vertical planes 66. Overlapping of the first electrodes 61 and the second electrodes 62 with the edges of the vibrating films 58 is avoided as much as possible. The first electrodes 61 and the second electrodes 62 do not hinder the vibration of the vibrating films 58. Similarly, the width of the first electrodes 61 along the longitudinal direction of the grooves 64 and the width of the second electrodes 62 along the longitudinal direction of the grooves 64 in plan view are smaller than the width of the piezoelectric films 63 along the longitudinal direction of the grooves 64 in plan view. The piezoelectric films 63 are arranged only within the regions of the vibrating films 58. The piezoelectric films 63 do not hinder the vibration of the vibrating films 58.

In the receiving array RR, within each individual column, the second electrode 62 of a first piezoelectric element 57 is connected to the first electrode 61 of an adjacent first piezoelectric element 57. One column of the first piezoelectric elements 57 is electrically connected in series. As such, the voltage generated by a deformation is increased and the sensitivity is enhanced.

As described above, in the ultrasonic device 17, the first piezoelectric elements 57 can be utilized for when ultrasonic waves are being received, and the second piezoelectric elements 23 can be utilized for when ultrasonic waves are being emitted. The first piezoelectric elements 57 have a higher sensitivity than the second piezoelectric elements 23, and therefore the ultrasonic resolution is enhanced.

(6) Method of Manufacturing First Ultrasonic Transducer Element

Figure 8:
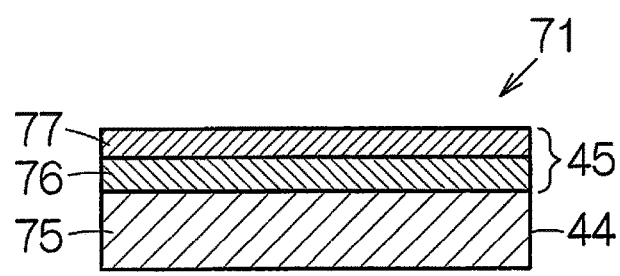
FIG. 8 is a step for manufacturing a first ultrasonic transducer element, and is an enlarged cross-sectional view of a substrate.

Next, a method of manufacturing a first piezoelectric element 57 shall be described in brief. A substrate 75 is prepared, as is illustrated in FIG. 8. The substrate 75 is formed of, for example, silicon. Formed on the surface of the substrate 75 are a silicon oxide layer 76 and a zirconium oxide layer 77. When the silicon oxide layer 76 is being formed, it suffices, for example, for the surface of the substrate 75 to undergo a heat treatment. The silicon of the substrate 75 is oxidized and forms silicon oxide. When the zirconium oxide layer 77 is being formed, a zirconium film is formed at uniform thickness. The zirconium film undergoes an oxidation treatment. In this manner, the substrate 44 and the coating film 45 are obtained.

Figure 9:
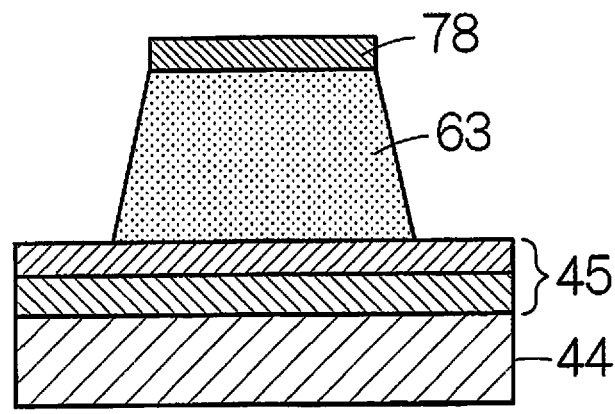
FIG. 9 is a step for manufacturing the first ultrasonic transducer element, and is an enlarged cross-sectional view of the substrate schematically illustrating a piezoelectric film and an underlying electroconductive film.

The piezoelectric film 63 and an underlying electroconductive film 78 are formed on the surface of the coating film 45, as illustrated in FIG. 9. The underlying electroconductive film 78 is patterned by upon a piezoelectric material film of a solid film. Next, the piezoelectric material film is subjected to etching. The piezoelectric film 63 is formed from the piezoelectric material film. The underlying electroconductive film 78 is layered onto the uppermost surface of the piezoelectric film 63.

Figure 10:
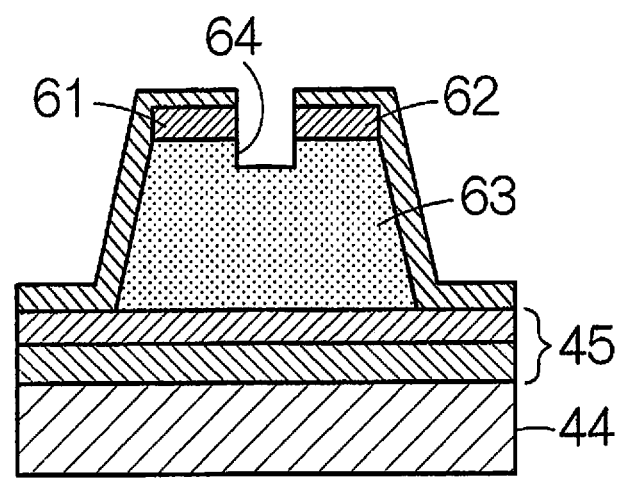
FIG. 10 is a step for manufacturing the first ultrasonic transducer element, and is an enlarged cross-sectional view of the substrate schematically illustrating a first electrode and a second electrode.

As illustrated in FIG. 10, an electrode film of a solid film is formed upon the underlying electroconductive film 78. The electrode film is exposed to an etching treatment. The first electrode 61, the second electrode 62, the third electroconductor 67, and the fourth electroconductor 68 are formed from the electrode film, in accordance to a defined patterning. At this time, the groove 64 is formed in accordance with over-etching between the first electrode 61 and the second electrode 62 on the uppermost surface of the piezoelectric film 63. The first electrode 61 and the second electrode 62 are separated in response to the formation of the groove 64. Thereafter, the opening section 46 is formed on the substrate 75, from a reverse surface.

(7) Verification of First Ultrasonic Transducer Element

Figure 11:
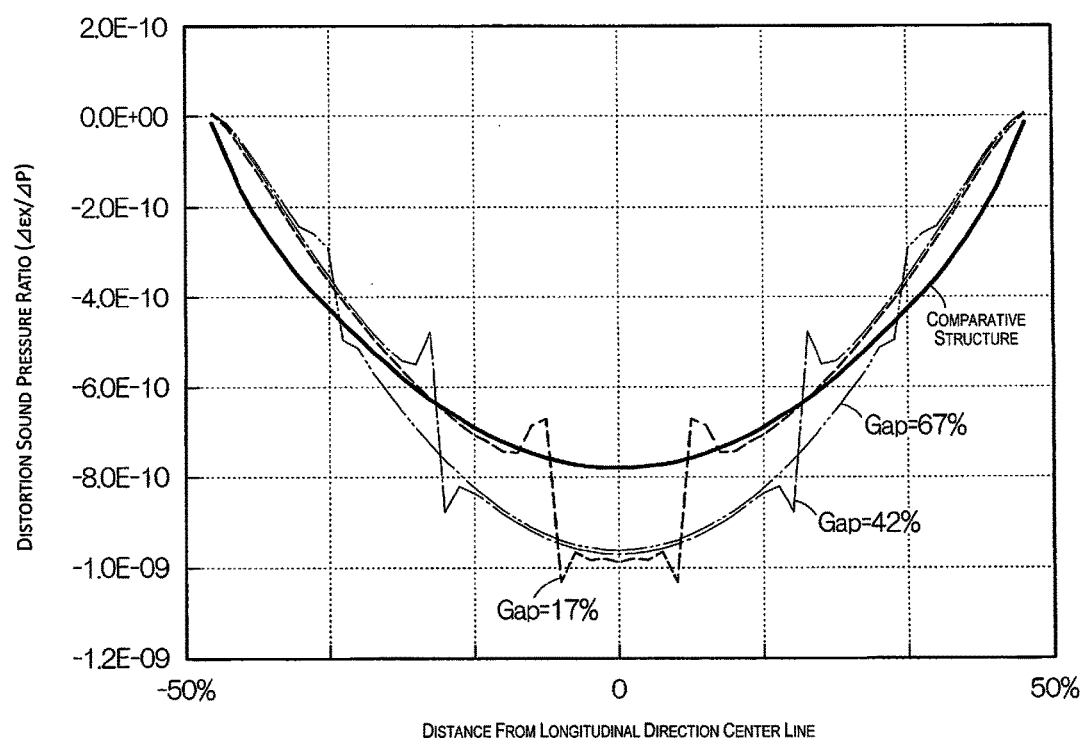
FIG. 11 is a graph illustrating a distortion sound pressure ratio in accordance with a distance from a longitudinal center line of a vibrating film.

The present inventors have verified the action of the groove 64 on the piezoelectric film 63. In the verification, the magnitude of distortion with respect to the sound pressure (the distortion sound pressure ratio) was calculated. In the calculation, a vibrating film having an aspect ratio of 10:1 was set. The width Wt of the groove was set to 17%, 42%, and 67% with respect to the width of the vibrating film 24. As a comparative example, a vibrating film without a groove for the piezoelectric film was prepared. FIG. 11 shows the manner in which the distortion sound pressure ratio of the vibrating film changes depending on the distance from a center line from the longitudinal direction. With the groove, it was confirmed that the distortion increases in accordance with a decrease in the thickness of the piezoelectric film. Moreover, it was discovered that when the groove was present, distortion is suppressed more near the edge of the vibrating film as compared to when the groove was absent.

Figure 12A:
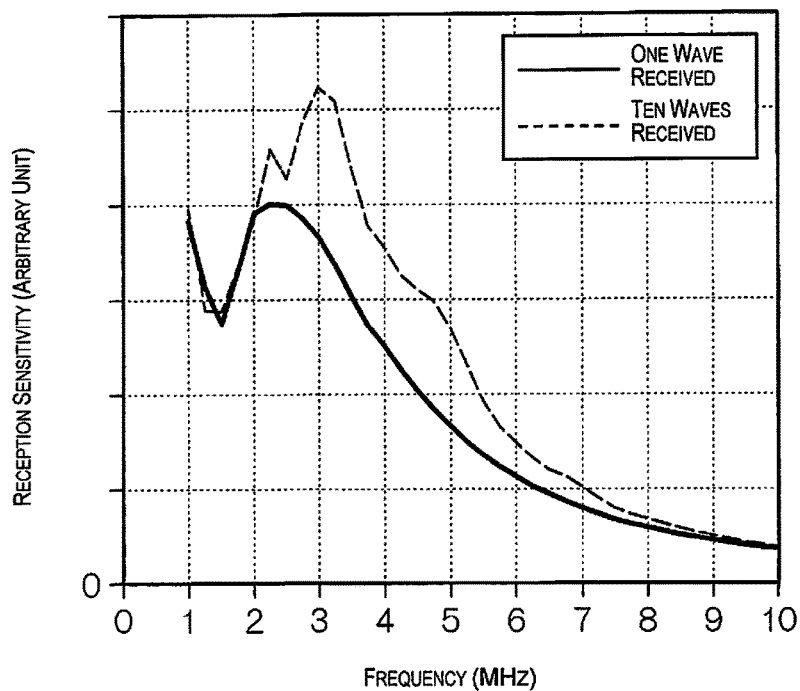
FIG. 12A is a graph illustrating a reception sensitivity with the structure of a first piezoelectric element.
Figure 12B:
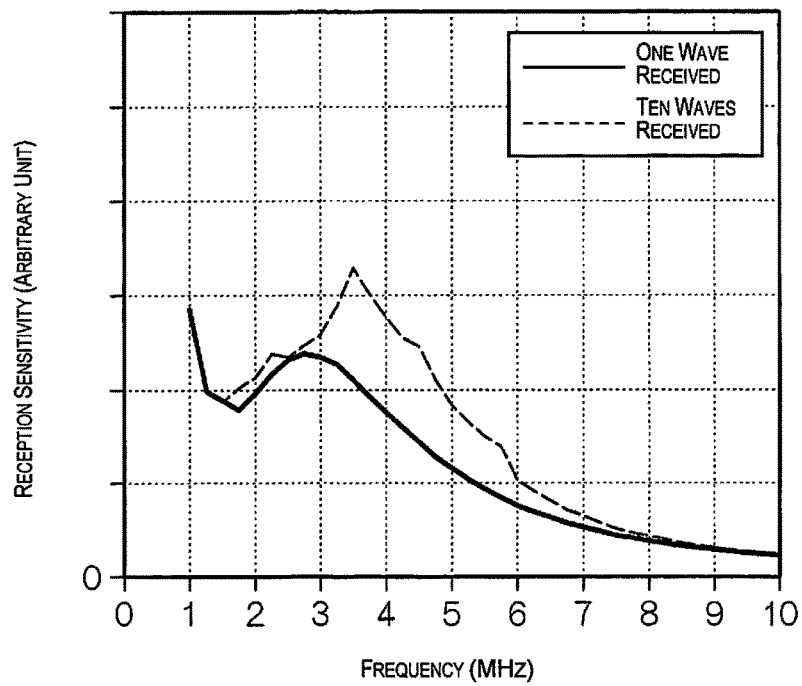
FIG. 12B is a graph illustrating a reception sensitivity with the structure of a second piezoelectric element.

The present inventors have verified the reception sensitivity of the first piezoelectric element. In the verification, the present inventors fabricated a first piezoelectric element. One sine wave (or ten waves) was inputted at a frequency of 1 to 10 MHz to a hydrophone, and the voltage that was generated in the first piezoelectric element when the ultrasonic wave generated in the water was received at the first piezoelectric element was measured. The present inventors prepared a comparative example. In the comparative example, a structure similar to that of the second piezoelectric element was established. As illustrated in FIGS. 12A and 12B, the first piezoelectric element was confirmed to have a higher reception sensitivity than that of the second piezoelectric element.

Figure 13:
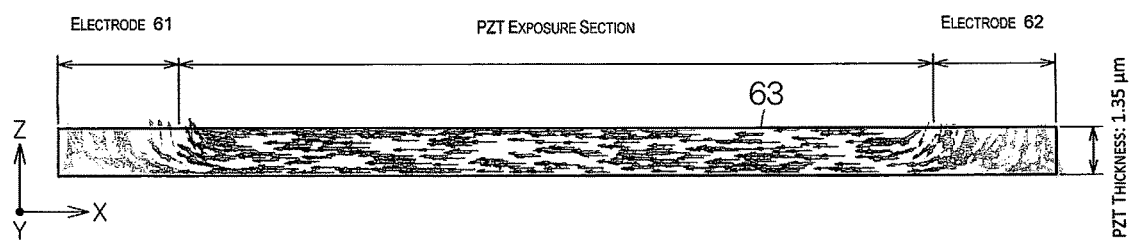
FIG. 13 is an image of a simulation schematically illustrating the appearance of lines of electric force flowing through the piezoelectric film.

Additionally, the present inventors have verified the lines of electric force in the piezoelectric film 63 with the first piezoelectric element. In the verification, a computer simulation was performed. The results, as illustrated in FIG. 13, confirm that the lines of electric force are evenly distributed throughout the piezoelectric film 63, even when the first electrode 61 and the second electrode 62 are installed on the uppermost surface of the piezoelectric film 63. As such, the usefulness of the structure as in the first piezoelectric elements 57 has been confirmed.

Figure 14:
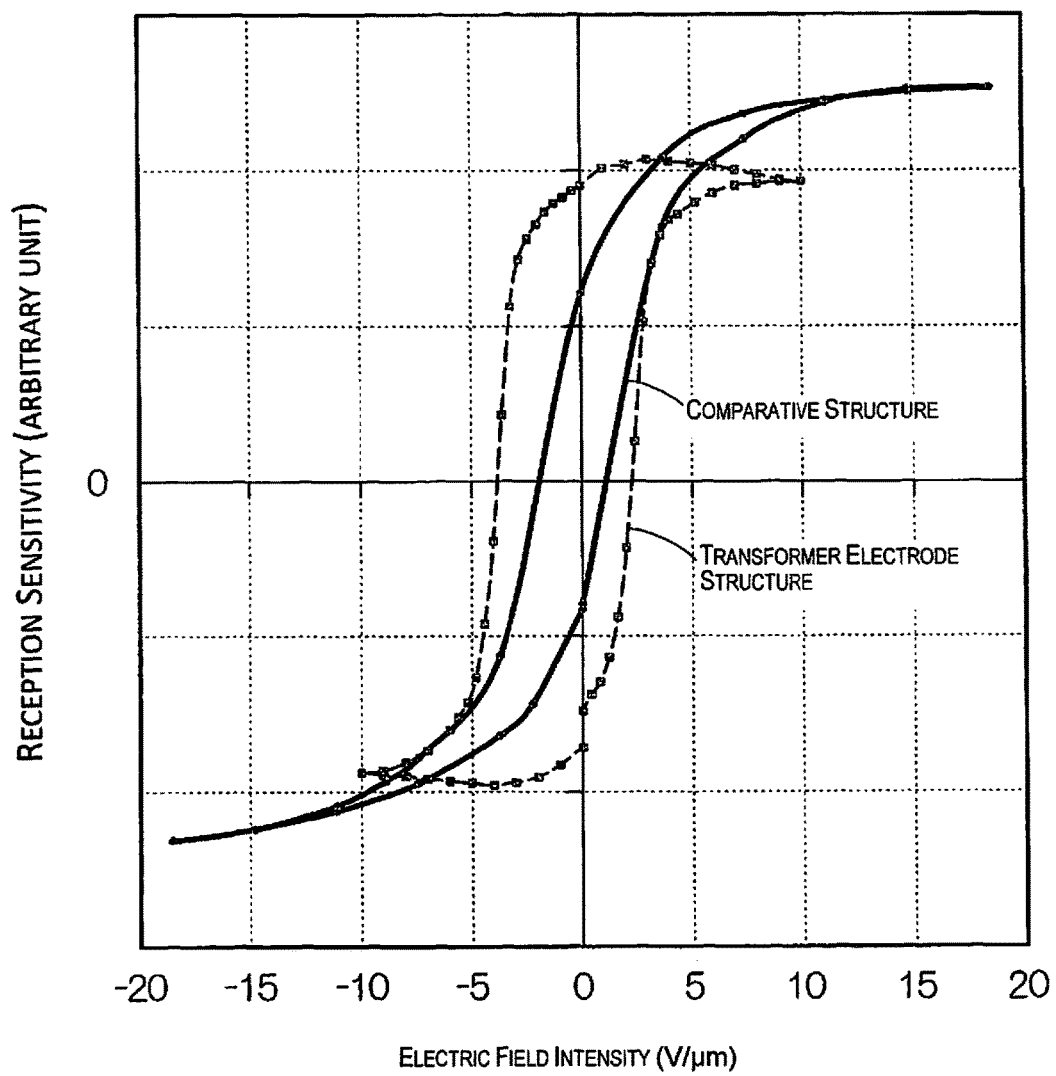
FIG. 14 is a graph illustrating a hysteresis loop of an electric field intensity.

The present inventors have moreover verified the magnitude of the residual polarization with the first piezoelectric element. In the verification, a computer simulation was performed. The present inventors prepared a comparative example. In the comparative example, a structure similar to that of the second piezoelectric element was established. As illustrated in FIG. 14, the first piezoelectric element was confirmed to yield a greater residual polarization than that of the structure of the second piezoelectric element. Thus, when sufficient polarization remains, then provided that a polarization process has been performed once, the application of a polarization voltage can be omitted (or can be reduced) at the time of generation of the piezoelectric effect. When the first piezoelectric elements 57 are connected in series as described above, a high polarization voltage is required when the piezoelectric films 63 are being polarized, but when a large residual polarization is ensured in this manner, the application of a polarization voltage at the time of receipt of the ultrasonic waves can be omitted, and it is possible to contribute to a reduction in power consumption.

Figure 15:
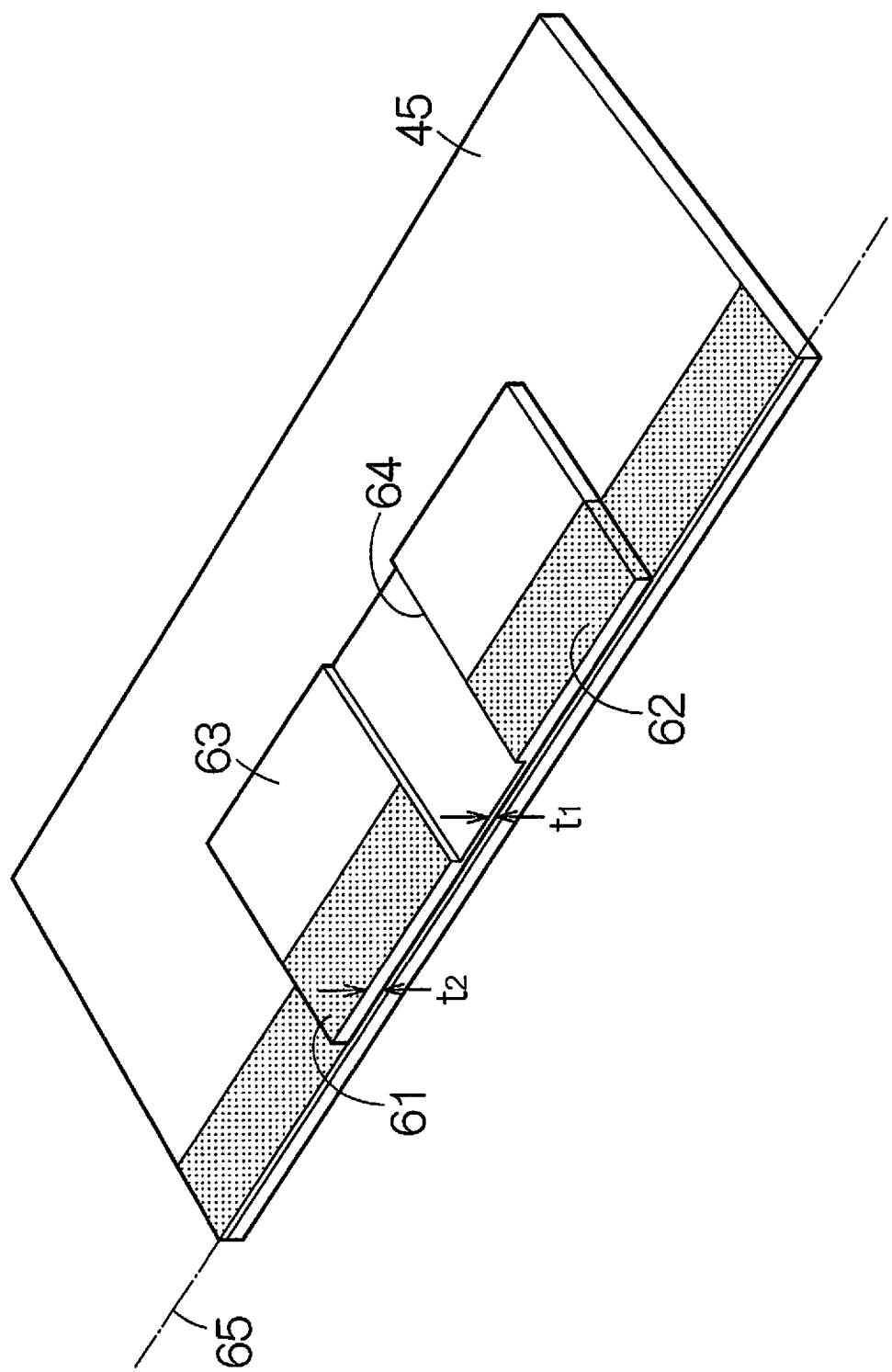
FIG. 15 is a perspective view illustrating one example of a simulation model.

The present inventors have observed the reception sensitivity of the first piezoelectric element while also varying the depth Dt of the groove 64. In the observation, a computer simulation was performed. The present inventors constructed a simulation model, as is illustrated in FIG. 15. Because the first piezoelectric elements 57 are formed in line symmetry with respect to the straight lines 65, the simulation model was constructed on one side of the straight lines 65. The vibrating film 24 and the piezoelectric film 63 were formed in a square outline. The width Wt of the groove 64 separating the electrode 61 and the electrode 62 was set to 6 μm. The film thickness of the silicon oxide layer 48 was set to 1,070 nm. The film thickness of the zirconium oxide layer 49 was set to 400 nm. A thickness $t_1$ of the piezoelectric film 63 as identified by the groove 64 was set to 270 nm. In the changing of the depth Dt, a thickness $t_2$ of the piezoelectric film 63 as identified elsewhere other than the groove 64 was changed. The film thickness of the first electrode 61 and of the second electrode 62 was set to 50 nm. The film thickness and thicknesses $t_1$, $t_2$ were all identified in the thickness direction of the vibrating film 24.

Figure 16:
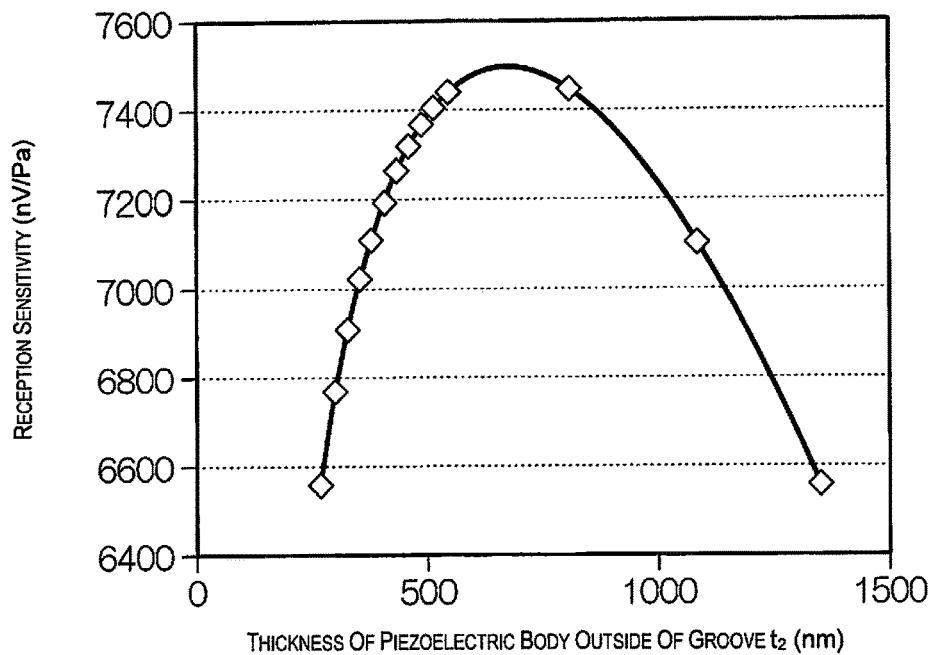
FIG. 16 is a graph illustrating a relationship between a thickness $t_2$ of a piezoelectric film outside a groove and a reception sensitivity.

As illustrated in FIG. 16, when the thickness $t_2$ increased elsewhere other than the groove 64 and the depth Dt of the groove 64 increased, then the reception sensitivity was confirmed to be higher. However, when the thickness $t_2$ exceeded 675 nm, then it was confirmed that the reception sensitivity decreased. When the thickness $t_2$ reached 1,350 nm, then it was confirmed that the reception sensitivity returned to being equivalent to that of a piezoelectric film 63 having a uniform thickness $t_2$ (i.e., not having a groove).

Figure 17:
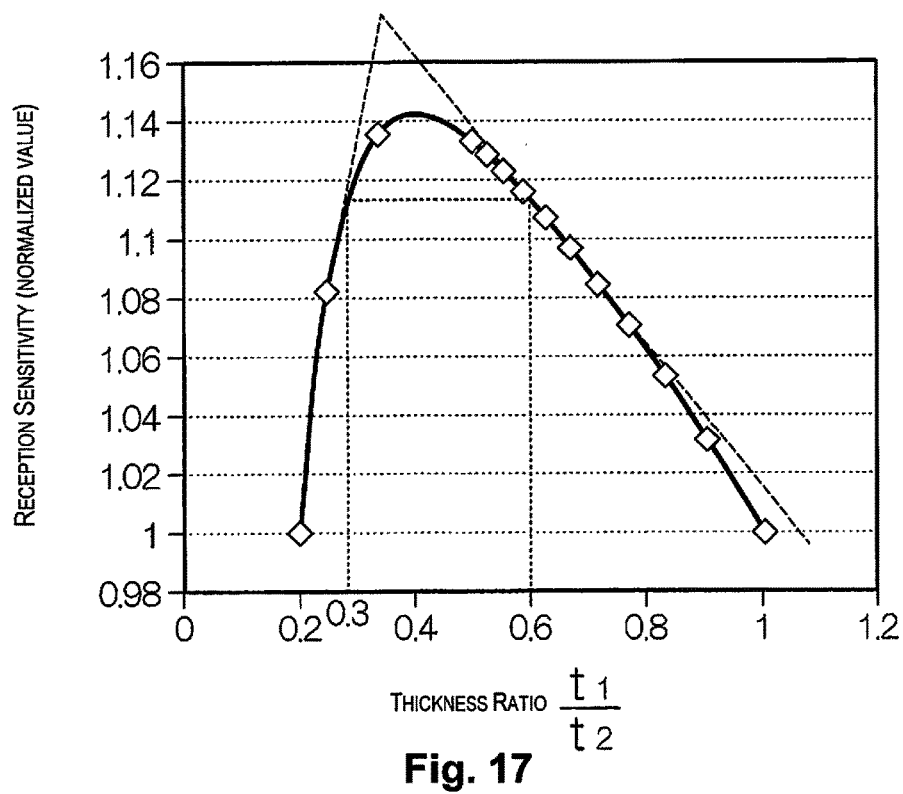
FIG. 17 is a graph illustrating a relationship between a thickness ratio ($=t_1/t_2$) and a reception sensitivity (normalized value)

As illustrated in FIG. 17, when the thickness ratio ($=t_1/t_2$) falls below 0.2, then it is easily assumed that the reception sensitivity would decrease further than that of a piezoelectric film of a uniform thickness $t_2$. As such, it was confirmed that when the following relationship holds true, the distortion is concentrated in the groove and the effect of the groove is achieved.

$$0.2 \leq \frac{t_1}{t_2} < 1.0$$

As can be interpreted from FIG. 17, it is expected that when the thickness ratio begins decreasing from 1.0 until the thickness ratio reaches 0.6, the change in reception sensitivity (normalized) is simply governed by the influence of the thickness ratio, i.e., by the effects of the formation of the groove 64. That is to say, the formation of a groove-shaped structure at a middle position in the vibrating film 24 causes stress from sound pressure to be concentrated in the region of the groove 64, increases the in-plane distortion of the piezoelectric film 63 between the first electrode 61 and the second electrode 62, and consequently increases the voltage caused by the piezoelectric effect. When the thickness ratio falls below 0.6, however, then it has been discovered that the increase in a factor that hinders the enhancement of the reception sensitivity, namely, the thickness $t_2$ of the piezoelectric film 63 under the electrodes, causes an effect whereby the overall structure of the piezoelectric element 57 becomes harder to begin to have an impact. This means that when the depth Dt of the groove 64 is simply increased, the reception sensitivity is not necessarily enhanced, and there is an optimum range for Dt that optimizes the reception sensitivity. The range is defined by the ratio between the thickness $t_1$ of the piezoelectric film 63 of the groove 64 and the thickness $t_2$ of the piezoelectric film 63 under the electrodes. FIG. 17 confirms that when the following formula holds true, the groove 64 contributes effectively to enhancing the reception sensitivity.

$$0.3 \leq \frac{t_1}{t_2} \leq 0.6$$

As is apparent from FIG. 17, when the thickness ratio reaches 0.4, it was confirmed that the reception sensitivity has been maximally improved. When the thickness ratio falls below 0.4, a decrease in the reception sensitivity was observed. The greater the depth Dt when the groove 64 is being formed, the greater the increase in the processing time for the formation. The throughput is adversely affected. Additionally, there is an increase in the volume of piezoelectric material that is removed. As such, provided that the thickness ratio is set at 0.4 or higher, the throughput can be maximally improved.

Figure 18:
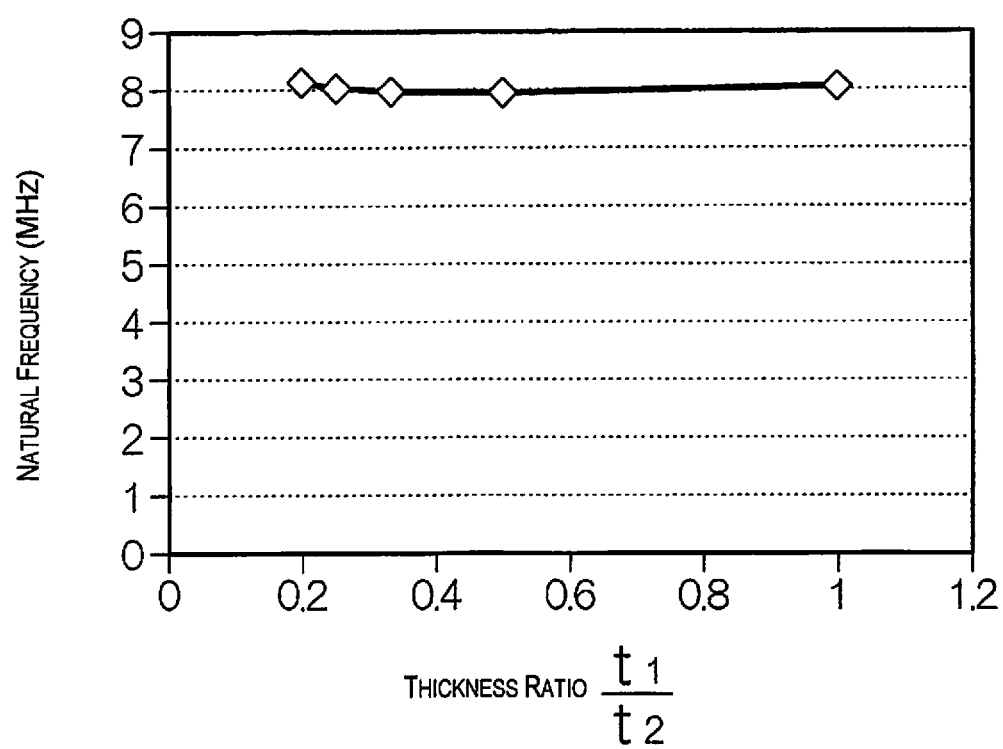
FIG. 18 is a graph illustrating a relationship between the thickness ratio ($=t_1/t_2$) and a natural frequency.

As is illustrated in FIG. 18, it was confirmed that even when the thickness ratio changes, the natural frequency of the vibrating film 24 does not change by any more than 1 MHz. As such, even when the groove 64 is formed on the piezoelectric film 63 to create a means for improving the reception sensitivity, it was found that the vibration properties of the piezoelectric element 57 do not vary provided that the groove formation is done within the range of the present embodiment. The natural frequency is inversely proportional to the wavelength of the sound waves, and the spatial resolution of the piezoelectric element 57 is decided on via the wavelength, so lowering the natural frequency would lead to a lowering of the resolution. Therefore, it would not be preferable for there to be a decrease in the natural frequency, in terms of the design of the element, even when this is done for a structure of the piezoelectric element 57 by which the reception sensitivity is enhanced.

(8) Configuration of Receiving Array as in Second Embodiment

Figure 19:
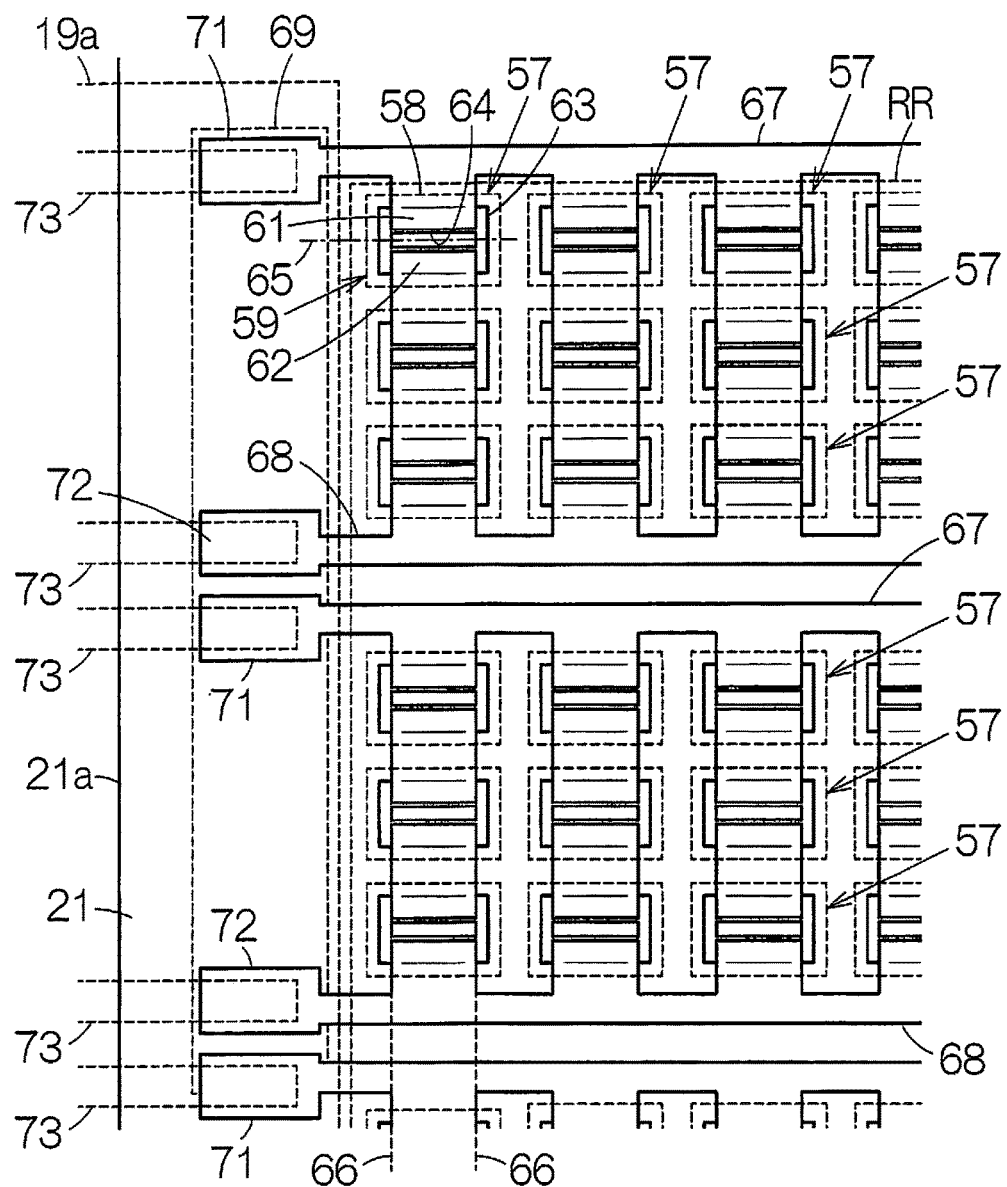
FIG. 19 is an enlarged partial plan view of an ultrasonic device schematically illustrating a region of a receiving array as in a second embodiment.

As is illustrated in FIG. 19, in the receiving array RR, the grooves 64 extend toward an edge of the piezoelectric films 63, outwardly from between the first electrodes 61 and the second electrodes 62, and are interrupted between the edges of the piezoelectric films 63 and spaces between the first electrodes 61 and the second electrodes 62. The grooves 64 do extend to the outside of the virtual vertical planes 66, but do not reach the edges of the piezoelectric films 63. In this manner, the grooves 64 do not completely traverse across the one surface of the piezoelectric films 63. In such a case, too, the piezoelectric films 63 have a decrease in thickness locally between the electrodes 61, 62, and therefore the distortion of the piezoelectric films 63 is concentrated to the paths of the lines of electric force between the electrodes 61, 62, thus making it possible for the piezoelectric effect to be utilized efficiently.

(9) Ultrasonic Diagnostic Apparatus as in Another Embodiment

Figure 20:
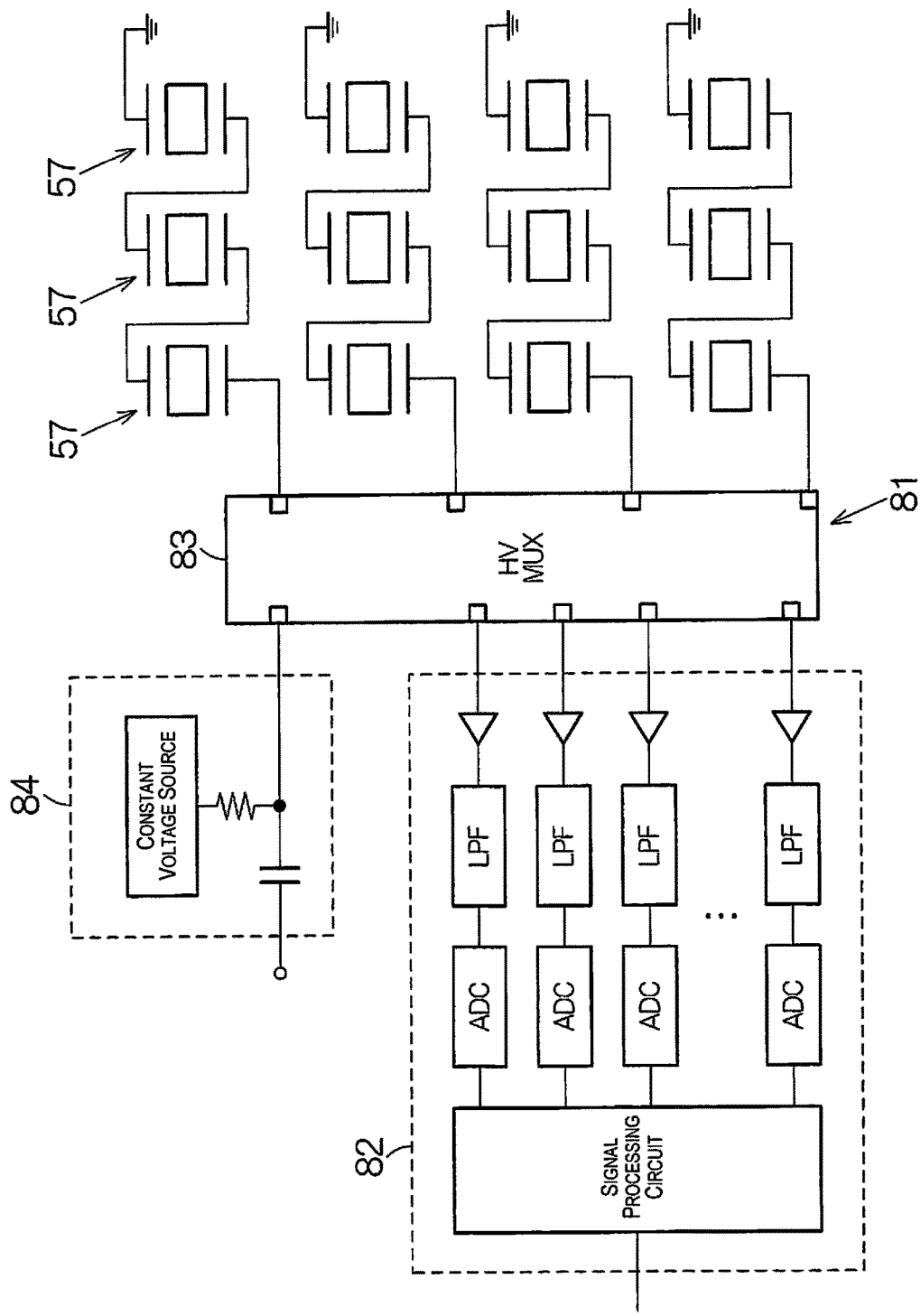
FIG. 20 is a block diagram schematically illustrating a circuit configuration of an ultrasonic diagnostic apparatus as in another embodiment.

FIG. 20 schematically illustrates a circuit configuration of an ultrasonic diagnostic apparatus 11 as in another embodiment. The ultrasonic diagnostic apparatus 11 is provided with an integrated circuit chip 81 that is electrically connected to the receiving array RR of the ultrasonic device 17. The integrated circuit chip 81 is provided with a receiver circuit 82, a multiplexer (switch) 83, and a polarization circuit 84. The multiplexer 83 selectively connects the receiver circuit 82 and the polarization circuit 84 to the first piezoelectric element 57 group. The receiver circuit 82 receives voltage on the basis of the piezoelectric effect from the first piezoelectric elements 57, which are connected to the paired third electroconductors 67 and fourth electroconductors 68. Ultrasonic waves are detected in accordance with the voltage received. The polarization circuit 84 supplies a polarization voltage to each of the first piezoelectric elements 57. Herein, when the ultrasonic waves are being received, the polarization circuit 84 is separated from the first piezoelectric elements 57. The multiplexer 83 switches the connection of the receiver circuit 82 and the connection of the polarization circuit 84 to the first piezoelectric elements 57. It suffices for the polarization voltage to be supplied in a manner that is appropriate and in accordance with necessity.

Though embodiments have been described in greater detail above, it shall be readily understood by a person skilled in the art that there are numerous possible modifications which do not substantially depart from the novel matter and effects of the present invention. As such, the modification examples of such description are all also included in the scope of the present invention. For example, in the specification or in the drawings, a phrase that is mentioned at least once together with a different phrase of the same or broader meaning can be substituted with that different phrase at any point in the specification or drawings as well. The configurations and operations of the ultrasonic diagnostic apparatus 11 are not limited to what was described in the present embodiments, nor are those of the apparatus terminal 12, the ultrasonic probe 13, the display panel 15, the housing 16, the acoustic lens 18, the first and second wiring boards 19a, 19b, the base 21, the second piezoelectric elements 23, the acoustic matching layer 51, and so forth; rather, a variety of modifications are possible.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A piezoelectric element comprising:
   a substrate including an opening section;
   a vibrating film arranged upon the substrate so as to overlap the opening section as seen in plan view from a thickness direction of the vibrating film;
   a piezoelectric body arranged upon the vibrating film so as to overlap the opening section as seen in the plan view;
   a first electrode arranged upon the piezoelectric body;
   a second electrode arranged upon the piezoelectric body and at a position that is separated from the first electrode; and
   a groove located between the first electrode and the second electrode and overlapping the opening section as seen in the plan view, the groove splitting a surface of the piezoelectric body in two as seen in the plan view.

2. The piezoelectric element as set forth in claim 1, wherein
   the groove extends toward an edge of the piezoelectric body, outwardly from between the first electrode and the second electrode, and traverses across one surface of the piezoelectric body.

3. The piezoelectric element as set forth in claim 1, wherein
   the groove extends toward an edge of the piezoelectric body, outwardly from between the first electrode and the second electrode, and is interrupted between the edge of the piezoelectric body and a space between the first electrode and the second electrode.

4. The piezoelectric element as set forth in claim 1, wherein
   the groove extends along a hypothetical straight line that passes through a center of gravity of the vibrating film as seen in the plan view.

5. The piezoelectric element as set forth in claim 4, wherein
   the vibrating film is formed in a shape of a rectangle as seen in the plan view, and the groove extends in parallel to any one side of the rectangle.

6. The piezoelectric element as set forth in claim 4, wherein
the piezoelectric body is formed in line symmetry with respect to the hypothetical straight line as seen in the plan view.

7. The piezoelectric element as set forth in claim 1, further comprising
a protective film having a lower Young's modulus than the piezoelectric body and formed on the groove.

8. The piezoelectric element as set forth in claim 7, wherein
the protective film is an acoustic matching layer with which the groove is filled.

9. The piezoelectric element as set forth in claim 1, wherein
a width of the first electrode along a longitudinal direction of the groove and a width of the second electrode along the longitudinal direction of the groove as seen in the plan view are smaller than a width of the piezoelectric body along the longitudinal direction of the groove as seen in the plan view.

10. The piezoelectric element as set forth in claim 9, wherein
the piezoelectric body is arranged only within a region of the vibrating film, as seen in the plan view.

11. The piezoelectric element as set forth in claim 1, wherein
a relationship of $$0.2 \le \frac{t_1}{t_2} < 1.0$$

holds true between $t_1$ that is a thickness of the piezoelectric body defined with the groove in the thickness direction, and $t_2$ that is a thickness of the piezoelectric body defined elsewhere other than the groove in the thickness direction.

12. The piezoelectric element as set forth in claim 11, wherein
a relationship of $$0.3 \le \frac{t_1}{t_2} \le 0.6$$

further holds true between the $t_1$ and the $t_2$.

13. The piezoelectric element as set forth in claim 11, wherein
a relationship of $$0.4 \le \frac{t_1}{t_2}$$

further holds true between the $t_1$ and the $t_2$.

14. A piezoelectric device comprising:
the piezoelectric element as set forth in claim 1;
a second vibrating film;
a second piezoelectric body arranged upon the second vibrating film;
a third electrode arranged upon the second piezoelectric body;
a fourth electrode arranged upon the second piezoelectric body and at a position that is separated from the third electrode;
a second groove located between the third electrode and the fourth electrode and splitting a surface of the second piezoelectric body in two, as seen in plan view from a thickness direction of the second vibrating film; and
an electroconductor section electrically connecting the second electrode and the third electrode together.

15. A piezoelectric device comprising:
the piezoelectric element as set forth in claim 1;
a second vibrating film;
a third electrode arranged upon the second vibrating film;
a second piezoelectric body arranged upon the third electrode; and
a fourth electrode arranged upon the second piezoelectric body.

16. A probe comprising a plurality of piezoelectric elements as set forth in claim 1.

17. A probe comprising a plurality of piezoelectric devices as set forth in claim 14.

18. A probe comprising a plurality of piezoelectric devices as set forth in claim 15.

19. An electronic machine comprising a plurality of piezoelectric elements as set forth in claim 1.

20. An electronic machine comprising a plurality of piezoelectric devices as set forth in claim 14.

21. An electronic machine comprising a plurality of piezoelectric devices as set forth in claim 15.

22. The electronic machine as set forth in claim 19, further comprising
a polarization circuit connected to the piezoelectric elements and configured to supply a polarization voltage to the piezoelectric elements;
a receiver circuit connected to the piezoelectric elements and configured to receive a voltage based on a piezoelectric effect from the piezoelectric elements; and
a switch configured to switch connections of the polarization circuit and the receiver circuit to the piezoelectric element.

23. An ultrasonic image apparatus comprising a plurality of piezoelectric elements as set forth in claim 1.

24. An ultrasonic image apparatus comprising a plurality of piezoelectric devices as set forth in claim 14.

25. An ultrasonic image apparatus comprising a plurality of piezoelectric devices as set forth in claim 15.

26. The ultrasonic image apparatus as set forth in claim 23, further comprising
a polarization circuit connected to the piezoelectric elements and configured to supply a polarization voltage to the piezoelectric elements;
a receiver circuit connected to the piezoelectric elements and configured to receive a voltage based on a piezoelectric effect from the piezoelectric elements; and
a switch configured to switch connections of the polarization circuit and the receiver circuit to the piezoelectric element.

27. A piezoelectric element comprising:
a substrate including an opening section
a vibrating film arranged upon the substrate so as to overlap the opening section as seen in plan view from a thickness direction of the vibrating film;
a piezoelectric body arranged upon the vibrating film so as to overlap the opening section as seen in the plan view;
a first signal electrode arranged upon one surface of the piezoelectric body;

a second signal electrode arranged upon the one surface of the piezoelectric body and at a position that is separated from the first signal electrode; and a groove located between the first signal electrode and the second signal electrode and overlapping the opening section as seen in the plan view, the groove reducing a thickness of the piezoelectric body in a direction orthogonal to a surface of the vibrating film.

\* \* \* \* \*